US008871998B2

(12) United States Patent
Noda et al.

(10) Patent No.: US 8,871,998 B2
(45) Date of Patent: Oct. 28, 2014

(54) METHOD FOR PRODUCING CHRYSANTHEMUM PLANT HAVING PETALS CONTAINING MODIFIED ANTHOCYANIN

(75) Inventors: Naonobu Noda, Tsukuba (JP); Ryutaro Aida, Tsukuba (JP); Sanae Sato, Tsukuba (JP); Akemi Ohmiya, Tsukuba (JP); Yoshikazu Tanaka, Osaka (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 393 days.

(21) Appl. No.: 13/265,791

(22) PCT Filed: Mar. 9, 2010

(86) PCT No.: PCT/JP2010/053909
§ 371 (c)(1),
(2), (4) Date: Nov. 30, 2011

(87) PCT Pub. No.: WO2010/122850
PCT Pub. Date: Oct. 28, 2010

(65) Prior Publication Data
US 2012/0073017 A1 Mar. 22, 2012

(30) Foreign Application Priority Data
Apr. 24, 2009 (JP) ................................. 2009-107055

(51) Int. Cl.
C12N 15/09 (2006.01)
C12N 15/63 (2006.01)
C12N 15/82 (2006.01)
C12N 5/04 (2006.01)
C12N 9/10 (2006.01)

(52) U.S. Cl.
CPC .......... *C12N 15/825* (2013.01); *C12N 15/8243* (2013.01); *C12N 9/1029* (2013.01)
USPC .......................... 800/287; 800/282; 800/323.2

(58) Field of Classification Search
None
See application file for complete search history.

(56) References Cited

U.S. PATENT DOCUMENTS

| 5,948,955 | A | 9/1999 | Holton et al. |
| 7,105,719 | B1 | 9/2006 | Ashikari et al. |
| 2011/0126320 | A1 | 5/2011 | Tanaka et al. |
| 2012/0073017 | A1 | 3/2012 | Noda et al. |

FOREIGN PATENT DOCUMENTS

| EP | 1652916 A1 | 5/2006 |
| JP | 2004/065096 A | 3/2004 |
| WO | 94/28140 | 12/1994 |
| WO | WO-94/28140 A1 | 12/1994 |
| WO | 96/25500 | 8/1996 |
| WO | WO-96/25500 A1 | 8/1996 |
| WO | WO-01/72984 A1 | 10/2001 |
| WO | 2004/020637 | 3/2004 |
| WO | 2005/017147 | 2/2005 |
| WO | Wo-2005/017147 A1 | 2/2005 |
| WO | 2009/062253 | 5/2009 |

OTHER PUBLICATIONS

Bevan et al. Tissue- and cell-specific activity of a phenylalanine ammonia-lyase promoter in transgenic plants. The EMBO Journal. 1989. 8(7): 1899-1906.*
European Search Report dated May 15, 2013 issued in Application No. 13157273.7-1406.
Tanaka, Y., et al., "Genetic Engineering in Floriculture," Plant Cell, Tissue and Organ Culture, Kluwer Academic Publishers, DO, vol. 80, No. 1, Jan. 1, 2005, pp. 1-24.
Aida, R., et al., "Modification of Flower Color in Torenia (*Torenia fournieri* Lind.) by Genetic Transformation," Plant Science, Elsevier Ireland, Ltd., IE, vol. 153, No. 1, Apr. 14, 2000, pp. 33-42.
Teixeira, Da Silva, J.A., "Chrysanthemum: Advances in Tissue Culture, Cryopreservation, Postharvest Technology, Genetics and Transgenic Biotechnology," Biotechnology Advances, Elsevier Publishing, Barking, GB, vol. 21, No. 8, Nov. 1, 2003, pp. 715-766.
Tanaka et al., "Biosynthesis of plant pigments: anthocyanins, betalains and carotenoids," Plant Journal, (2008), vol. 54, pp. 733-749.
Kondo et al., "Structure of Malonylshisonin, a Genuine Pigment in Purple Leaves of *Perilla ocimoides* L. var. *crispa* Benth," Agric. Biol. Chem., vol. 53, No. 3, pp. 797-800 (1989).
Mitsuhara et al., "Efficient Promoter Cassettes for Enhanced Expression of Foreign Genes in Dicotyledonous and Monocotyledonous Plants," Plant Cell Physiol., vol. 37, No. 1, pp. 49-59 (1996).

(Continued)

*Primary Examiner* — Brent T Page
*Assistant Examiner* — Ashley K Buran
(74) *Attorney, Agent, or Firm* — Drinker Biddle & Reath LLP

(57) ABSTRACT

Disclosed are a method for controlling flavonoid synthesis in a *chrysanthemum* plant or non-*chrysanthemum* plant by genetic recombination technology using a transcriptional regulatory region useful for altering flower color, a method for modifying anthocyanins, a method for producing a *chrysanthemum* plant or non-*chrysanthemum* plant containing modified anthocyanins in the petals thereof, and a *chrysanthemum* plant or non-*chrysanthemum* plant, progeny thereof, or vegetatively propagated products, part or tissue thereof transformed with the regulatory region. In the method according to the present invention, an expression vector or expression cassette containing a transcriptional regulatory region of perilla anthocyanin 3-acyltransferase gene, such as a nucleic acid containing the nucleotide sequence indicated in SEQ ID NO. 1, or a transcriptional regulatory region of pansy F3'5'H gene, such as the nucleotide sequence indicated in SEQ ID NO. 15, is used.

6 Claims, 7 Drawing Sheets

(56) References Cited

OTHER PUBLICATIONS

Comai et al., "Novel and useful properties of a chimeric plant promoter combining CaMV 35S and MAS elements," Plant Molecular Biology, vol. 15, pp. 373-381, (1990).
Stam et al., "The Silence of Genes in Transgenic Plants," Annals of Botany, vol. 79, pp. 3-12, (1997).
Nozaki et al., "Effects of high temperature on flower colour and anthocyanin content in pink flower genotypes of greenhouse chrysanthemum (*Chrysanthemum morifolium* Ramat.)," Journal of Horticultural Science & Biotechnology (2006), vol. 81, No. 4, pp. 728-734.
Takatsu et al., "Transgene inactivation in *Agrobacterium*-mediated chrysanthemum (*Dendranthema grandiflorum* (Ramat.) Kitamura) transformants," Plant Biotechnology, vol. 17, No. 3, pp. 241-245 (2000).
Aida et al., "Efficient Transgene Expression in Chrysanthemum, *Dendranthema grandiflorum* (Ramat.) Kitamura, by Using the Promoter of a Gene for Chrysanthemum Chlorophyll-a/b-binding Protein," Breeding Science, Vo. 54, pp. 51-58, (2004).
Aida et al., "Efficient Transgene Expression in Chrysanthemum, *Chrysanthemum morifolium* Ramat., with the Promoter of a Gene for Tobacco Elongation Factor 1 α Protein," JARQ, vol. 39, No. 4, pp. 269-274 (2005).
Narumi et al., "Transformation of chrysanthemum with mutated ethylene receptor genes: *mDG-ERS1* transgenes conferring reduced ethylene sensitivity and characterization of the transformants," Postharvest Biology and Technology, vol. 27, (2005) pp. 101-110.
Aida et al., "Chrysanthemum flower shape modification by suppression of chrysanthemum-*Agamous* gene," Plant Biotech., vol. 25, pp. 55-59, (2008).
Aida et al., "Improved translation efficiency in chrysanthemum and torenia with a translational enhancer derived from the tobacco *alcohol dehydrogenase* gene," Plant Biotechnology, vol. 25, pp. 69-75, (2008).
Courtney-Gutterson et al., "Modification of Flower Color in Florist's Chrysanthemum: Production of a White-Flowering Variety Through Molecular Genetics," Bio/Technology, vol. 12, Mar. 1994, pp. 268-271.
Ohmiya et al., "Carotenoid Cleavage Dioxygenase (CmCCD4a) Contributes to White Color Formation in Chrysanthemum Petals," Plant Physiology, Nov. 2006, vol. 142, pp. 1193-1201.
Seo et al., "Co-expression of flavonoid 3', 5'-*hydroxylase* and flavonoid 3'-*hydroxylase* Accelerates Decolorization in Transgenic Chrysanthemum Petals," Journal of Plant Biology, Dec. 2007, vol. 50, No. 6, pp. 626-631.
Annadana et al., "The potato *Lhca3.St.1* promoter confers high and stable transgene expression in chrysanthemum, in contrast to CaMV-based promoters," Molecular Breeding, vol. 8, pp. 335-344, (2001).
Annadana et al., "Cloning of the chrysanthemum *UEP1* promoter and comparative expression in florets and leaves of *Dendranthema grandiflora*," Transgenic Research, vol. 11, pp. 437-445, (2002).
U.S. Office Action dated Apr. 26, 2013 issued in U.S. Appl. No. 13/265,752.
Ø. Anderson, "Anthocyanins," Encyclopedia of Life Sciences, 2002, pp. 1-8.
Y. Kim et al., "A 20 nucleotide upstream element is essential for the nopaline synthase (*nos*) promoter activity," Plant Molecular Biology, 1994, vol. 24, pp. 105-117.
D. Kennell, "Principles and Practices of Nucleic Acid Hybridization," Progress in Nucleic Acid Research and Molecular Biology, 1971, vol. 11, pp. 259-301.
T. Maniatis et al., "Molecular Cloning," Cold Spring Harbor Laboratory, 1982, pp. 324-389.
A.G. Bovy et al., "Genetic Modification of the Vase-Life of Carnation," ACTA Horticulture, 1995, vol. 405, pp. 179-189.
U.S. Office Action dated Jul. 9, 2013 issued in U.S. Appl. No. 13/265,752.
U.S. Notice of Allowance dated Oct. 23, 2013 issued in U.S. Appl. No. 13/265,752.
Supplementary European Search Report; dated Oct. 5, 2012; Application No. EP10766909; 8-pages.
GSN: AWV66308; XP-002683026 Database Geneseq [Online]: "Viola flavonoid 3', 5' hydroxylase (F3'5'H) promoter, SEQ ID No. 18", XP002683026, retrieved from EBI accession No. GSN:AWV66308; Database accession No. AWV66308 "sequence"(2009).
International Search Report dated May 25, 2010 for International Application No. PCT/JP2010/053909 filed Mar. 9, 2010.
K. Yonekura-Sakakibara et al., "Molecular and Biochemical Characterization of a Novel Hydroxycinnamoyl-CoA: Anthocyanin 3-*O*-Glucoside-6"-*O*-Achyltransferase from *Perilla frutescens*", Plant Cell Physiol., 2000, vol. 41, p. 495-502.
J. Seo et al., "Co-expression of *flavonoid 3', 5'-hydroxylase* and *flavonoid 3'-hydroxylase* Accelerates Decolorization in Transgenic Chrysanthemum Petals", Journal of Plant Biology, Dec. 2007, vol. 50, p. 626-631.

\* cited by examiner

SEQUENCE LISTING

```
<160> NUMBER OF SEQ ID NOS: 31

<210> SEQ ID NO 1
<211> LENGTH: 1096
<212> TYPE: DNA
<213> ORGANISM: Perilla frutescens
<220> FEATURE:
<221> NAME/KEY: promoter
<222> LOCATION: (1)..(1096)
<223> OTHER INFORMATION: anthocyanin 3-acyl transferase promoter
```

-continued

<400> SEQUENCE: 1

```
aactattatg atcccacaga gtttttgaca gatgagtctt caggaggaga tgctgaacct    60
tttcactact ctactgaacg catcacaagt ttatcggctt atatgactaa tagggatcaa   120
cttcacaaca gagaggctca tagagctctt aaagaggatt tgatcgagca catatggaaa   180
aaattcggca ctaactaaat atataattta cgttttatgc actcgtaatt taaaatttca   240
tgtgtctcat tgtagtttat ttaattatgt tttcactctt gtaatttta tttttgttgtg   300
aagtaaatta tgaatttata attatatggg taattttttg ataattatgc aattaaaaat   360
aattaatatt ttttaaatgc aagagaaaaa tgttatttta ataacatgtt cttattaaaa   420
aataaaatga taaatatttt atgtaggttg ggagaaaatg aaaaaataat atttatttg    480
aaggttgggt tggatgaggt cactgatggg agtataaata atactccctc cgtcccataa   540
ttattgtcca ttattccttt tgggatgtc ccaaaattat agtcctattc taaattggga    600
ttgtatttaa atattctttt acaaatataa ccctatttga tatagtatga atgcaattaa   660
tatagtaaaa aaataagggc aatataggat aattattgta aattgtatat ttccaataca   720
tattaaatgt gatttcttaa tctgtgtgaa aataggaagt ggactataat tatgggacgg   780
agggagtata aagttggagg ttgtggatgt ggaggagaaa gaaattaata ttttatttaa   840
agattggatt aaaggaggtc actgatgtgg gtagtcttag aggaaatgta gtcttagagg   900
aaatctgccc agcaaaataa aataataagt aaataaataa actaaatatg tattgaatgc   960
gacatctagc aatatagcca catatatagt gcagtagcac gcagcgctcg ttactcgtca  1020
gtcgtcaaag aatggtaagt atagaaaagc atctttaaat aacacaccaa aaaccacagc  1080
tacgttcaac accgcc                                                  1096
```

<210> SEQ ID NO 2
<211> LENGTH: 4087
<212> TYPE: DNA
<213> ORGANISM: Perilla frutescens
<220> FEATURE:
<221> NAME/KEY: CDS
<222> LOCATION: (1097)..(2443)
<223> OTHER INFORMATION: pSPB3311, anthocyanin 3-acyl transferase
      promoter + CDS + terminator

<400> SEQUENCE: 2

```
aactattatg atcccacaga gtttttgaca gatgagtctt caggaggaga tgctgaacct    60
tttcactact ctactgaacg catcacaagt ttatcggctt atatgactaa tagggatcaa   120
cttcacaaca gagaggctca tagagctctt aaagaggatt tgatcgagca catatggaaa   180
aaattcggca ctaactaaat atataattta cgttttatgc actcgtaatt taaaatttca   240
tgtgtctcat tgtagtttat ttaattatgt tttcactctt gtaatttta tttttgttgtg   300
aagtaaatta tgaatttata attatatggg taattttttg ataattatgc aattaaaaat   360
aattaatatt ttttaaatgc aagagaaaaa tgttatttta ataacatgtt cttattaaaa   420
aataaaatga taaatatttt atgtaggttg ggagaaaatg aaaaaataat atttatttg    480
aaggttgggt tggatgaggt cactgatggg agtataaata atactccctc cgtcccataa   540
ttattgtcca ttattccttt tgggatgtc ccaaaattat agtcctattc taaattggga    600
ttgtatttaa atattctttt acaaatataa ccctatttga tatagtatga atgcaattaa   660
tatagtaaaa aaataagggc aatataggat aattattgta aattgtatat ttccaataca   720
tattaaatgt gatttcttaa tctgtgtgaa aataggaagt ggactataat tatgggacgg   780
```

-continued

```
agggagtata aagttggagg ttgtggatgt ggaggagaaa gaaattaata ttttatttaa      840
agattggatt aaaggaggtc actgatgtgg gtagtcttag aggaaatgta gtcttagagg      900
aaatctgccc agcaaaataa aataataagt aaataaataa actaaatatg tattgaatgc      960
gacatctagc aatatagcca catatatagt gcagtagcac gcagcgctcg ttactcgtca     1020
gtcgtcaaag aatggtaagt atagaaaagc atctttaaat aacacaccaa aaaccacagc     1080
tacgttcaac accgcc atg acc acc acc gtg atc gaa acg tgt aga gtt ggg    1132
              Met Thr Thr Thr Val Ile Glu Thr Cys Arg Val Gly
                1               5                   10 cca ccg ccg gac tcg gtg gcg gag caa tcg ttg ccg ctc aca ttc ttc      1180
Pro Pro Pro Asp Ser Val Ala Glu Gln Ser Leu Pro Leu Thr Phe Phe
         15                  20                  25 gac atg acg tgg ctg cat ttt cat ccc atg ctt cag ctc ctc ttc tac      1228
Asp Met Thr Trp Leu His Phe His Pro Met Leu Gln Leu Leu Phe Tyr
 30                  35                  40 gaa ttc cct tgt tcc aag caa cat ttc tca gaa tcc atc att cca aaa      1276
Glu Phe Pro Cys Ser Lys Gln His Phe Ser Glu Ser Ile Ile Pro Lys
45                  50                  55                  60 ctc aaa caa tct ctc tct aaa act ctc ata cac ttc ttc cct ctc tca      1324
Leu Lys Gln Ser Leu Ser Lys Thr Leu Ile His Phe Phe Pro Leu Ser
                 65                  70                  75 tgc aat tta atc tac cct tca tct ccg gag aaa atg ccc gag ttt cgg      1372
Cys Asn Leu Ile Tyr Pro Ser Ser Pro Glu Lys Met Pro Glu Phe Arg
         80                  85                  90 tat cta tcg ggg gac tcg gtt tct ttc act atc gca gaa tct agc gac      1420
Tyr Leu Ser Gly Asp Ser Val Ser Phe Thr Ile Ala Glu Ser Ser Asp
         95                 100                 105 gac ttc gat gat ctc gtc gga aat cgc gca gaa tct ccc gtt agg ctc      1468
Asp Phe Asp Asp Leu Val Gly Asn Arg Ala Glu Ser Pro Val Arg Leu
110                 115                 120 tac aac ttc gtc cct aaa ttg ccg cag att gtc gaa gaa tct gat aga      1516
Tyr Asn Phe Val Pro Lys Leu Pro Gln Ile Val Glu Glu Ser Asp Arg
125                 130                 135                 140 aaa ctc ttc caa gtt ttc gcc gtg cag gtg act ctt ttc cca ggt cga      1564
Lys Leu Phe Gln Val Phe Ala Val Gln Val Thr Leu Phe Pro Gly Arg
                145                 150                 155 ggc gtc ggt att gga ata gca acg cat cac acc gtt agc gat gcc ccg      1612
Gly Val Gly Ile Gly Ile Ala Thr His His Thr Val Ser Asp Ala Pro
                160                 165                 170 tcg ttt ctc gcc ttt ata acg gct tgg gct tgg atg agc aaa cac att      1660
Ser Phe Leu Ala Phe Ile Thr Ala Trp Ala Trp Met Ser Lys His Ile
        175                 180                 185 gaa gat gaa gat gaa gag ttt aaa tct ttg cca gtt ttc gat aga tcc      1708
Glu Asp Glu Asp Glu Glu Phe Lys Ser Leu Pro Val Phe Asp Arg Ser
190                 195                 200 gtc ata aaa tat ccg acg aaa ttt gac tcg att tat tgg aaa aag gcg      1756
Val Ile Lys Tyr Pro Thr Lys Phe Asp Ser Ile Tyr Trp Lys Lys Ala
205                 210                 215                 220 cta aaa ttt cct ttg caa tct cgt cat ccc tca tta ccg acg gac cgc      1804
Leu Lys Phe Pro Leu Gln Ser Arg His Pro Ser Leu Pro Thr Asp Arg
                225                 230                 235 att cga acc acg ttc gtt ttc acc caa tcc gaa att aag aaa ttg aag      1852
Ile Arg Thr Thr Phe Val Phe Thr Gln Ser Glu Ile Lys Lys Leu Lys
            240                 245                 250 ggt tcg att cag tcc aga gtt cca agt tta gtc cat ctc tca tct ttt      1900
Gly Ser Ile Gln Ser Arg Val Pro Ser Leu Val His Leu Ser Ser Phe
            255                 260                 265 gta gcg att gca gct tat atg tgg gct ggc gta acg aaa tca ctc aca      1948
```

|  |  |  |  |  |  |  |  |  |  |  |  |  |  |
|---|---|---|---|---|---|---|---|---|---|---|---|---|---|
| Val | Ala | Ile | Ala | Ala | Tyr | Met | Trp | Ala | Gly | Val | Thr | Lys | Ser | Leu | Thr |
|  |  | 270 |  |  | 275 |  |  |  |  | 280 |  |  |  |

```
gca gat gaa gac cac gac gac ggg gat gca ttt ttc ttg att ccg gtc    1996
Ala Asp Glu Asp His Asp Asp Gly Asp Ala Phe Phe Leu Ile Pro Val
285             290              295                  300 gat cta agg cca cga tta gat ccg cca gtt ccc gaa aat tac ttc ggg    2044
Asp Leu Arg Pro Arg Leu Asp Pro Pro Val Pro Glu Asn Tyr Phe Gly
            305              310                  315 aac tgc tta tcg tac gcg ctg ccg aga atg cgg cgg cga gag ctg gtg    2092
Asn Cys Leu Ser Tyr Ala Leu Pro Arg Met Arg Arg Arg Glu Leu Val
        320              325              330 gga gag aaa ggg gtg ttt ctg gcg gct gag gca atc gcg gcg gag atc    2140
Gly Glu Lys Gly Val Phe Leu Ala Ala Glu Ala Ile Ala Ala Glu Ile
            335              340              345 aaa aaa agg atc aac gac aag aga ata tta gaa acg gtg gag aaa tgg    2188
Lys Lys Arg Ile Asn Asp Lys Arg Ile Leu Glu Thr Val Glu Lys Trp
    350              355              360 tcg ctg gag att cgt gaa gcg ttg cag aaa tca tat ttt tcg gtg gca    2236
Ser Leu Glu Ile Arg Glu Ala Leu Gln Lys Ser Tyr Phe Ser Val Ala
365             370              375                  380 gga tcg agc aag cta gat ctt tac ggt gca gat ttt gga tgg ggg aag    2284
Gly Ser Ser Lys Leu Asp Leu Tyr Gly Ala Asp Phe Gly Trp Gly Lys
            385              390                  395 gcg aga aag caa gaa ata ttg tcg att gat ggg gag aaa tat gca atg    2332
Ala Arg Lys Gln Glu Ile Leu Ser Ile Asp Gly Glu Lys Tyr Ala Met
        400              405              410 acg ctt tgt aaa gcc agg gat ttc gaa gga gga ttg gag gtt tgc ttg    2380
Thr Leu Cys Lys Ala Arg Asp Phe Glu Gly Gly Leu Glu Val Cys Leu
            415              420              425 tct ttg cct aag gac aaa atg gat gct ttt gct gct tat ttt tca gcg    2428
Ser Leu Pro Lys Asp Lys Met Asp Ala Phe Ala Ala Tyr Phe Ser Ala
    430              435              440 gga att aat ggt taa taaatgtatg taattaaact aatattatta tgtaacaatt    2483
Gly Ile Asn Gly
445 aattaagtgt tgagtaacgt gaagaataat atcttttacc tattatatat ttatgagttg    2543 gttcaaataa aatcacttca tttattgtat taaccgttta gtgttcttct caccatattt    2603 tggtgctatt ttttaaaaaa tgttttttt attgtatttt agtattaatt gttttaccac    2663 taaaattaca gtaaaatgca agatagttta attttacat ttacatatga aacacattct    2723 ctttataacc aacctctcta tatatataat atgtgtgtat gtatgtatac acatgtatga    2783 atactagaaa tatatcttaa accatccatc cttcaaaaat ttcggggcca tattgcatgg    2843 tgacattata atatttgata atttcttcga acacgttatt aattcaattt ataattcta    2903 ataaaaagac gctcagacaa tatatgtaga taggatcggc ccaaaggggt gtctgggtgg    2963 gctgtcgccc atgggccccg aaatcttagg ggcaaaaaaa aaaaaattca ttatacctag    3023 ggcaaaaaaa ttaccgctct tcacttctct gcctctctcc ctcatccctc gttcctcctc    3083 tctcttccct atgtacgcct ctttcactcc ctcccctct ctcagttctc tatcacttgt    3143 attttgtatt gaaacttgt tgaaaactaa accaaaaata gaaaaggta tagaaaattt    3203 gaaaacaaag gttgtttttt tgtgttgctg cagttcccaa acttgccgag ttgccgactt    3263 gccgtgttga attgttatat atgttaaaag cctaaaatat atcctttcag aattgagatg    3323 gattgttgta actatcaggt ttttttatt gagaatttta gatcaattag ttatcttgta    3383 attttttatt cttttaata caatactccc tccatcccaa tagcaaggtc cccttgctat    3443
```

-continued

```
tgggcacggg tattaaggag gaggattatt ataatgaaaa ttaatataaa gtaagtggat    3503
tccactttat taaggaatat tataatcaaa agtaatataa agtaagtgga ttccacttta    3563
attaggacac taattatttt ctttttttggt atgagacttt gctattggga catcccaaaa   3623
aggcaaaaga gaccttgcta ttaggacggt ggacgtgctg ccgaggcacg caaattaatt    3683
tacctttcct cttctatact aactcgtagt agcggcgagt aaaggtcgaa ccctcaagga    3743
gcaattgaac tagatgtgct attagaaata aaataaacac aagtgagagg ggagtttttg    3803
gtttcaattt aactaaaact aattatgaaa atgaaaaaac aaatataaaa cataaacagg    3863
tagacgaaat atgataaaga tagaattcta gttctcggtt cagttatcac ctttctccaa    3923
gtatttcatg aataatgcaa cgcctctttt catacaactt agaatcgatg tccaaaggtt    3983
aatatcaagc tttatttacc taattgtctc gtacgattag ttaactaaaa caagctcttt    4043
aattaactct actcaattag ataacctaga ataagctctc taga                    4087
```

<210> SEQ ID NO 3
<211> LENGTH: 448
<212> TYPE: PRT
<213> ORGANISM: Perilla frutescens

<400> SEQUENCE: 3

```
Met Thr Thr Thr Val Ile Glu Thr Cys Arg Val Gly Pro Pro Asp
1               5                   10                  15

Ser Val Ala Glu Gln Ser Leu Pro Leu Thr Phe Phe Asp Met Thr Trp
            20                  25                  30

Leu His Phe His Pro Met Leu Gln Leu Leu Phe Tyr Glu Phe Pro Cys
        35                  40                  45

Ser Lys Gln His Phe Ser Glu Ser Ile Ile Pro Lys Leu Lys Gln Ser
    50                  55                  60

Leu Ser Lys Thr Leu Ile His Phe Phe Pro Leu Ser Cys Asn Leu Ile
65                  70                  75                  80

Tyr Pro Ser Ser Pro Glu Lys Met Pro Glu Phe Arg Tyr Leu Ser Gly
                85                  90                  95

Asp Ser Val Ser Phe Thr Ile Ala Glu Ser Ser Asp Asp Phe Asp Asp
            100                 105                 110

Leu Val Gly Asn Arg Ala Glu Ser Pro Val Arg Leu Tyr Asn Phe Val
        115                 120                 125

Pro Lys Leu Pro Gln Ile Val Glu Glu Ser Asp Arg Lys Leu Phe Gln
    130                 135                 140

Val Phe Ala Val Gln Val Thr Leu Phe Pro Gly Arg Gly Val Gly Ile
145                 150                 155                 160

Gly Ile Ala Thr His His Thr Val Ser Asp Ala Pro Ser Phe Leu Ala
                165                 170                 175

Phe Ile Thr Ala Trp Ala Trp Met Ser Lys His Ile Glu Asp Glu Asp
            180                 185                 190

Glu Glu Phe Lys Ser Leu Pro Val Phe Asp Arg Ser Val Ile Lys Tyr
        195                 200                 205

Pro Thr Lys Phe Asp Ser Ile Tyr Trp Lys Lys Ala Leu Lys Phe Pro
    210                 215                 220

Leu Gln Ser Arg His Pro Ser Leu Pro Thr Asp Arg Ile Arg Thr Thr
225                 230                 235                 240

Phe Val Phe Thr Gln Ser Glu Ile Lys Lys Leu Lys Gly Ser Ile Gln
                245                 250                 255

Ser Arg Val Pro Ser Leu Val His Leu Ser Ser Phe Val Ala Ile Ala
```

|  |  |  | 260 |  |  |  | 265 |  |  |  | 270 |  |  |
|---|---|---|---|---|---|---|---|---|---|---|---|---|---|
| Ala | Tyr | Met | Trp | Ala | Gly | Val | Thr | Lys | Ser | Leu | Thr | Ala | Asp | Glu | Asp |
|  |  |  | 275 |  |  |  | 280 |  |  |  | 285 |  |  |

His Asp Asp Gly Asp Ala Phe Phe Leu Ile Pro Val Asp Leu Arg Pro
    290                        295                        300

Arg Leu Asp Pro Pro Val Pro Glu Asn Tyr Phe Gly Asn Cys Leu Ser
305                        310                        315                        320

Tyr Ala Leu Pro Arg Met Arg Arg Glu Leu Val Gly Glu Lys Gly
                        325                        330                        335

Val Phe Leu Ala Ala Glu Ala Ile Ala Ala Glu Ile Lys Lys Arg Ile
                  340                        345                        350

Asn Asp Lys Arg Ile Leu Glu Thr Val Glu Lys Trp Ser Leu Glu Ile
                  355                        360                        365

Arg Glu Ala Leu Gln Lys Ser Tyr Phe Ser Val Ala Gly Ser Ser Lys
                  370                        375                        380

Leu Asp Leu Tyr Gly Ala Asp Phe Gly Trp Gly Lys Ala Arg Lys Gln
385                      390                        395                        400

Glu Ile Leu Ser Ile Asp Gly Glu Lys Tyr Ala Met Thr Leu Cys Lys
                  405                        410                        415

Ala Arg Asp Phe Glu Gly Gly Leu Glu Val Cys Leu Ser Leu Pro Lys
                  420                        425                        430

Asp Lys Met Asp Ala Phe Ala Ala Tyr Phe Ser Ala Gly Ile Asn Gly
                  435                        440                        445

<210> SEQ ID NO 4
<211> LENGTH: 6835
<212> TYPE: DNA
<213> ORGANISM: Perilla frutescens
<220> FEATURE:
<221> NAME/KEY: CDS
<222> LOCATION: (1608)..(2330)
<223> OTHER INFORMATION: Other ORF
<220> FEATURE:
<221> NAME/KEY: CDS
<222> LOCATION: (3439)..(4785)
<223> OTHER INFORMATION: SAT208 ORF
<220> FEATURE:
<221> NAME/KEY: misc_feature
<222> LOCATION: (6815)..(6815)
<223> OTHER INFORMATION: n is a, c, g, or t

<400> SEQUENCE: 4

| | | | | | |
|---|---|---|---|---|---|
| ccccaaaaac | cttgattagg | gtgatggttc | acgtagtggg | ccatcgccct | gatagacggt | 60 |
| ttttcgccct | tgacgttgg | agtccacgtt | ctttaatagt | ggactcttgt | tccaaactgg | 120 |
| aacaacactc | aaccctatct | cggtctattc | ttttgattta | taagggattt | tgccgatttc | 180 |
| ggcctattgg | ttaaaaaaat | gagctgattt | aacaaaaatt | taacgcgaat | tttaacaaaa | 240 |
| tattaacgct | tacaatttcc | attcgccatt | caggctgcgc | aactgttggg | aagggcgatc | 300 |
| ggtgcgggcc | tcttcgctat | tacgccagct | ggcgaaaggg | ggatgtgctg | caaggcgatt | 360 |
| aagttgggta | acgccagggt | tttcccagtc | acgacgttgt | aaaacgacgg | ccagtgagcg | 420 |
| cgcgtaatac | gactcactat | agggcgaatt | gggtaccggg | cccccctcg | aggtcgacgg | 480 |
| tatcgataag | cttgatatcg | aattcctgca | gcccggggga | tccactagtt | ctagaagatg | 540 |
| aagagacaaa | acatcgacta | cttgcccttg | tgtttgggca | aaattaaatt | aatgtaattg | 600 |
| taattgtgag | atgtgtgtta | gtaattatgc | tatgtgtgtg | ttagtaatta | tgagatgtgt | 660 |
| gtgtttgtaa | ttttgagatg | tcttttcctc | actttataaa | taattaatgt | attttatgca | 720 |

```
tatctatttc tcttattctt ttcatacaaa cctgcatgca taagtctcaa tcatgcattg    780
gattctttat gccttgtcaa tttcttttg tacaaacctc atgcatctca atcatgcatt    840
ggattcttat actctcattt caatttatat gcaagagtaa agctaagtat atcacatgca    900
ttggattcca ctttatatca aattgatttc ttgataaatc acatgctttt gtcagccatc    960
acatgcattg gattccactt tatatcaaat taatttcttg ataaatcaca tacttttgtc   1020
ggccatttca tgcattggat tccactttat atcaaattga tttttgata atcacatgc    1080 ttttgtcggc tagcccatgc tttgtctata catatctcag aaaatgcaca tcaaaagaaa   1140
ctcaaacaaa atcctcaata ccttaccaca tctttcaact tcactttaga aaaatgtctg   1200
cacatgaaaa ttctgatgtt gaatcaaact caagttctaa ttattctgat ctaacgaac    1260 ttgatgaatg ctagagcga ggttatgaaa atatcgtga agttgatagt ataatccaga    1320
atgtgctcat aaataatccc aatctggttg taggagctca aacttctaca gtcagaagaa   1380
ggtattgtga tagggaacgt gagaatggtg aagagcgttt gatgaaagac tattttgtct   1440
ctaatccaac gtattctcca gagctcttcc gacgatgatt tcacatgcag aaatcacttt   1500
ttcttcgtat agtggaggcc gttactacca atgatgacta ttttcaacag aggccaaatt   1560
gcacgggtag aaaaggtctt tcaccattgt aaaaatgtac aggagct atg agg gta   1616
                                                    Met Arg Val
                                                      1 ttg gct tat ggg gca tca gcc gat gtc gtt gat gaa tac tta cga atg    1664
Leu Ala Tyr Gly Ala Ser Ala Asp Val Val Asp Glu Tyr Leu Arg Met
  5              10                  15 agt gca acg gta aca aga gat gct gtc atc cat ttc gta gaa ggt gtc    1712
Ser Ala Thr Val Thr Arg Asp Ala Val Ile His Phe Val Glu Gly Val
 20              25                  30                  35 att tca tgc ttc agt gac aca tat ctt agg aag cct aat caa caa gat    1760
Ile Ser Cys Phe Ser Asp Thr Tyr Leu Arg Lys Pro Asn Gln Gln Asp
         40                  45                  50 ttg gca aga cta ctc tat gtt gga gag caa cgt ggt ttt cct ggc atg    1808
Leu Ala Arg Leu Leu Tyr Val Gly Glu Gln Arg Gly Phe Pro Gly Met
             55                  60                  65 att ggt agt att gat tgc atg cac tgg gaa tgg aca aat tgt cct aat    1856
Ile Gly Ser Ile Asp Cys Met His Trp Glu Trp Thr Asn Cys Pro Asn
         70                  75                  80 gcc tgg gca ggg caa ttt aca ggg aga agt gga aag tca aca atc att    1904
Ala Trp Ala Gly Gln Phe Thr Gly Arg Ser Gly Lys Ser Thr Ile Ile
 85                  90                  95 ttg gaa gct gtt gca tca tat gat tta tgg ata tgg cat gcg ttt ttt    1952
Leu Glu Ala Val Ala Ser Tyr Asp Leu Trp Ile Trp His Ala Phe Phe
100                 105                 110                 115 gga aca tca ggt gcg tgc aat gat att aat gtt ctc cac ggt tct cca    2000
Gly Thr Ser Gly Ala Cys Asn Asp Ile Asn Val Leu His Gly Ser Pro
            120                 125                 130 att ttt agt gat gtt tta gaa ggt cga gca cca cat gtt agt tac atc    2048
Ile Phe Ser Asp Val Leu Glu Gly Arg Ala Pro His Val Ser Tyr Ile
            135                 140                 145 gtc aat ggt cgc caa aat gat aga gca tat tat ctc acc gat ggc ata    2096
Val Asn Gly Arg Gln Asn Asp Arg Ala Tyr Tyr Leu Thr Asp Gly Ile
        150                 155                 160 tat cct tca tgg gct gca ttt gta aag tca atc aca tct cct atg act    2144
Tyr Pro Ser Trp Ala Ala Phe Val Lys Ser Ile Thr Ser Pro Met Thr
        165                 170                 175 cga aag tat aag ttg ttt gtt caa cac caa gaa gct gct aga aaa gat    2192
Arg Lys Tyr Lys Leu Phe Val Gln His Gln Glu Ala Ala Arg Lys Asp
180                 185                 190                 195
```

```
gta gaa cgg gcc ttt gga gtt cta caa gct cgt ttt gca ttt att cga    2240
Val Glu Arg Ala Phe Gly Val Leu Gln Ala Arg Phe Ala Phe Ile Arg
            200                 205                 210 cgt cca tgt ctt gtt tgg gac aag gtt ttg atg gga aaa att atg atg    2288
Arg Pro Cys Leu Val Trp Asp Lys Val Leu Met Gly Lys Ile Met Met
        215                 220                 225 gct tgt atc atc ata cac aat atg att gtg gag gat gaa tga            2330
Ala Cys Ile Ile Ile His Asn Met Ile Val Glu Asp Glu
                230                 235                 240 gacacatacc taaactatta tgatcccaca gagtttttga cagatgagtc ttcaggagga   2390
gatgctgaac cttttcacta ctctactgaa cgcatcacaa gttatcggc ttatatgact   2450 aatagggatc aacttcacaa cagagaggct catagagctc ttaaagagga tttgatcgag  2510
cacatatgga aaaaattcgg cactaactaa atatataatt tacgttttat gcactcgtaa  2570
tttaaaattt catgtgtctc attgtagttt atttaattat gttttcactc ttgtaatttt  2630
tattttgttg tgaagtaaat tatgaattta aattatatg ggtaattttt tgataattat   2690
gcaattaaaa ataattaata ttttttaaat gcaagagaaa aatgttattt taataacatg  2750
ttcttattaa aaaataaaat gataaatatt ttatgtaggt tgggagaaaa tgaaaaaata  2810 atatttatt tgaaggttgg gttggatgag gtcactgatg ggagtataaa taatactccc   2870
tccgtcccat aattattgtc cattattcct ttttgggatg tcccaaaatt atagtcctat  2930
tctaaattgg gattgtattt aaatattctt ttacaaatat aaccctatttt gatatagtat 2990 gaatgcaatt aatatagtaa aaaaataagg gcaatatagg ataattattg taaattgtat  3050
atttccaata catattaaat gtgatttctt aatctgtgtg aaaataggaa gtggactata  3110
attatgggac ggagggagta taagttgga ggttgtggat gtggaggaga aagaaattaa   3170 tatttattt aaagattgga ttaaaggagg tcactgatgt gggtagtctt agaggaaatg   3230
tagtcttaga ggaaatctgc ccagcaaaat aaaataataa gtaaataaat aaactaaata  3290
tgtattgaat gcgacatcta gcaatatagc cacatatata gtgcagtagc acgcagcgct  3350
cgttactcgt cagtcgtcaa agaatggtaa gtatagaaaa gcatctttaa ataacacacc  3410
aaaaaccaca gctacgttca acaccgcc atg acc acc acc gtg atc gaa acg     3462
                                Met Thr Thr Thr Val Ile Glu Thr
                                245 tgt aga gtt ggg cca ccg ccg gac tcg gtg gcg gag caa tcg ttg ccg    3510
Cys Arg Val Gly Pro Pro Pro Asp Ser Val Ala Glu Gln Ser Leu Pro
    250                 255                 260 ctc aca ttc ttc gac atg acg tgg ctg cat ttt cat ccc atg ctt cag    3558
Leu Thr Phe Phe Asp Met Thr Trp Leu His Phe His Pro Met Leu Gln
265                 270                 275                 280 ctc ctc ttc tac gaa ttc cct tgt tcc aag caa cat ttc tca gaa tcc    3606
Leu Leu Phe Tyr Glu Phe Pro Cys Ser Lys Gln His Phe Ser Glu Ser
            285                 290                 295 atc att cca aaa ctc aaa caa tct ctc tct aaa act ctc ata cac ttc    3654
Ile Ile Pro Lys Leu Lys Gln Ser Leu Ser Lys Thr Leu Ile His Phe
        300                 305                 310 ttc cct ctc tca tgc aat tta atc tac cct tca tct ccg gag aaa atg    3702
Phe Pro Leu Ser Cys Asn Leu Ile Tyr Pro Ser Ser Pro Glu Lys Met
                315                 320                 325 ccc gag ttt cgg tat cta tcg ggg gac tcg gtt tct ttc act atc gca    3750
Pro Glu Phe Arg Tyr Leu Ser Gly Asp Ser Val Ser Phe Thr Ile Ala
            330                 335                 340 gaa tct agc gac gac ttc gat gat ctc gtc gga aat cgc gca gaa tct    3798
Glu Ser Ser Asp Asp Phe Asp Asp Leu Val Gly Asn Arg Ala Glu Ser
```

|   |   |   |   |   |   |   |   |   |   |   |   |   |   |   |   |
|---|---|---|---|---|---|---|---|---|---|---|---|---|---|---|---|
| 345 |   |   |   | 350 |   |   |   | 355 |   |   |   | 360 |   |   |   |
| ccc | gtt | agg | ctc | tac | aac | ttc | gtc | cct | aaa | ttg | ccg | cag | att | gtc | gaa | 3846 |
| Pro | Val | Arg | Leu | Tyr | Asn | Phe | Val | Pro | Lys | Leu | Pro | Gln | Ile | Val | Glu |
|   |   |   |   |   | 365 |   |   |   | 370 |   |   |   | 375 |   |   |
| gaa | tct | gat | aga | aaa | ctc | ttc | caa | gtt | ttc | gcc | gtg | cag | gtg | act | ctt | 3894 |
| Glu | Ser | Asp | Arg | Lys | Leu | Phe | Gln | Val | Phe | Ala | Val | Gln | Val | Thr | Leu |
|   |   |   | 380 |   |   |   |   | 385 |   |   |   |   | 390 |   |   |
| ttc | cca | ggt | cga | ggc | gtc | ggt | att | gga | ata | gca | acg | cat | cac | acc | gtt | 3942 |
| Phe | Pro | Gly | Arg | Gly | Val | Gly | Ile | Gly | Ile | Ala | Thr | His | His | Thr | Val |
|   |   | 395 |   |   |   |   | 400 |   |   |   |   | 405 |   |   |   |
| agc | gat | gcc | ccg | tcg | ttt | ctc | gcc | ttt | ata | acg | gct | tgg | gct | tgg | atg | 3990 |
| Ser | Asp | Ala | Pro | Ser | Phe | Leu | Ala | Phe | Ile | Thr | Ala | Trp | Ala | Trp | Met |
|   | 410 |   |   |   |   | 415 |   |   |   |   | 420 |   |   |   |   |
| agc | aaa | cac | att | gaa | gat | gaa | gat | gaa | gag | ttt | aaa | tct | ttg | cca | gtt | 4038 |
| Ser | Lys | His | Ile | Glu | Asp | Glu | Asp | Glu | Glu | Phe | Lys | Ser | Leu | Pro | Val |
| 425 |   |   |   | 430 |   |   |   | 435 |   |   |   | 440 |   |   |   |
| ttc | gat | aga | tcc | gtc | ata | aaa | tat | ccg | acg | aaa | ttt | gac | tcg | att | tat | 4086 |
| Phe | Asp | Arg | Ser | Val | Ile | Lys | Tyr | Pro | Thr | Lys | Phe | Asp | Ser | Ile | Tyr |
|   |   |   |   | 445 |   |   |   | 450 |   |   |   | 455 |   |   |   |
| tgg | aaa | aag | gcg | cta | aaa | ttt | cct | ttg | caa | tct | cgt | cat | ccc | tca | tta | 4134 |
| Trp | Lys | Lys | Ala | Leu | Lys | Phe | Pro | Leu | Gln | Ser | Arg | His | Pro | Ser | Leu |
|   |   | 460 |   |   |   |   | 465 |   |   |   |   | 470 |   |   |   |
| ccg | acg | gac | cgc | att | cga | acc | acg | ttc | gtt | ttc | acc | caa | tcc | gaa | att | 4182 |
| Pro | Thr | Asp | Arg | Ile | Arg | Thr | Thr | Phe | Val | Phe | Thr | Gln | Ser | Glu | Ile |
|   | 475 |   |   |   |   | 480 |   |   |   |   | 485 |   |   |   |   |
| aag | aaa | ttg | aag | ggt | tcg | att | cag | tcc | aga | gtt | cca | agt | tta | gtc | cat | 4230 |
| Lys | Lys | Leu | Lys | Gly | Ser | Ile | Gln | Ser | Arg | Val | Pro | Ser | Leu | Val | His |
| 490 |   |   |   |   | 495 |   |   |   | 500 |   |   |   |   |   |   |
| ctc | tca | tct | ttt | gta | gcg | att | gca | gct | tat | atg | tgg | gct | ggc | gta | acg | 4278 |
| Leu | Ser | Ser | Phe | Val | Ala | Ile | Ala | Ala | Tyr | Met | Trp | Ala | Gly | Val | Thr |
| 505 |   |   |   | 510 |   |   |   | 515 |   |   |   | 520 |   |   |   |
| aaa | tca | ctc | aca | gca | gat | gaa | gac | cac | gac | gac | ggg | gat | gca | ttt | ttc | 4326 |
| Lys | Ser | Leu | Thr | Ala | Asp | Glu | Asp | His | Asp | Asp | Gly | Asp | Ala | Phe | Phe |
|   |   |   | 525 |   |   |   |   | 530 |   |   |   |   | 535 |   |   |
| ttg | att | ccg | gtc | gat | cta | agg | cca | cga | tta | gat | ccg | cca | gtt | ccc | gaa | 4374 |
| Leu | Ile | Pro | Val | Asp | Leu | Arg | Pro | Arg | Leu | Asp | Pro | Pro | Val | Pro | Glu |
|   |   | 540 |   |   |   |   | 545 |   |   |   |   | 550 |   |   |   |
| aat | tac | ttc | ggg | aac | tgc | tta | tcg | tac | gcg | ctg | ccg | aga | atg | cgg | cgg | 4422 |
| Asn | Tyr | Phe | Gly | Asn | Cys | Leu | Ser | Tyr | Ala | Leu | Pro | Arg | Met | Arg | Arg |
|   |   | 555 |   |   |   |   | 560 |   |   |   |   | 565 |   |   |   |
| cga | gag | ctg | gtg | gga | gag | aaa | ggg | gtg | ttt | ctg | gcg | gct | gag | gca | atc | 4470 |
| Arg | Glu | Leu | Val | Gly | Glu | Lys | Gly | Val | Phe | Leu | Ala | Ala | Glu | Ala | Ile |
|   | 570 |   |   |   |   | 575 |   |   |   |   | 580 |   |   |   |   |
| gcg | gcg | gag | atc | aaa | aaa | agg | atc | aac | gac | aag | aga | ata | tta | gaa | acg | 4518 |
| Ala | Ala | Glu | Ile | Lys | Lys | Arg | Ile | Asn | Asp | Lys | Arg | Ile | Leu | Glu | Thr |
| 585 |   |   |   | 590 |   |   |   | 595 |   |   |   | 600 |   |   |   |
| gtg | gag | aaa | tgg | tcg | ctg | gag | att | cgt | gaa | gcg | ttg | cag | aaa | tca | tat | 4566 |
| Val | Glu | Lys | Trp | Ser | Leu | Glu | Ile | Arg | Glu | Ala | Leu | Gln | Lys | Ser | Tyr |
|   |   |   | 605 |   |   |   |   | 610 |   |   |   |   | 615 |   |   |
| ttt | tcg | gtg | gca | gga | tcg | agc | aag | cta | gat | ctt | tac | ggt | gca | gat | ttt | 4614 |
| Phe | Ser | Val | Ala | Gly | Ser | Ser | Lys | Leu | Asp | Leu | Tyr | Gly | Ala | Asp | Phe |
|   |   | 620 |   |   |   |   | 625 |   |   |   |   | 630 |   |   |   |
| gga | tgg | ggg | aag | gcg | aga | aag | caa | gaa | ata | ttg | tcg | att | gat | ggg | gag | 4662 |
| Gly | Trp | Gly | Lys | Ala | Arg | Lys | Gln | Glu | Ile | Leu | Ser | Ile | Asp | Gly | Glu |
|   | 635 |   |   |   |   | 640 |   |   |   |   | 645 |   |   |   |   |
| aaa | tat | gca | atg | acg | ctt | tgt | aaa | gcc | agg | gat | ttc | gaa | gga | gga | ttg | 4710 |
| Lys | Tyr | Ala | Met | Thr | Leu | Cys | Lys | Ala | Arg | Asp | Phe | Glu | Gly | Gly | Leu |
| 650 |   |   |   | 655 |   |   |   | 660 |   |   |   |   |   |   |   |
| gag | gtt | tgc | ttg | tct | ttg | cct | aag | gac | aaa | atg | gat | gct | ttt | gct | gct | 4758 |

```
              Glu Val Cys Leu Ser Leu Pro Lys Asp Lys Met Asp Ala Phe Ala Ala
              665                 670                 675                 680 tat ttt tca gcg gga att aat ggt taa taaatgtatg taattaaact              4805
Tyr Phe Ser Ala Gly Ile Asn Gly
                685 aatattatta tgtaacaatt aattaagtgt tgagtaacgt gaagaataat atcttttacc      4865 tattatatat ttatgagttg gttcaaataa aatcacttca tttattgtat taaccgttta      4925 gtgttcttct caccatattt tggtgctatt ttttaaaaaa tgtttttttt attgtatttt      4985 agtattaatt gttttaccac taaaattaca gtaaaatgca agatagttta atttttacat      5045 ttacatatga aacacattct ctttataacc aacctctcta tatatataat atgtgtgtat      5105 gtatgtatac acatgtatga atactagaaa tatatcttaa accatccatc cttcaaaaat      5165 ttcggggcca tattgcatgg tgacattata atatttgata atttcttcga acacgttatt      5225 aattcaattt ataattcta ataaaaagac gctcagacaa tatatgtaga taggatcggc       5285 ccaaaggggt gtctgggtgg gctgtcgccc atgggccccg aaatcttagg ggcaaaaaaa      5345 aaaaaattca ttatacctag ggcaaaaaaa ttaccgctct tcacttctct gcctctctcc      5405 ctcatccctc gttcctcctc tctcttccct atgtacgcct ctttcactcc ctcccccctct    5465 ctcagttctc tatcacttgt attttgtatt gaaaacttgt tgaaaactaa accaaaaata     5525 gaaaaaggta tagaaaattt gaaaacaaag gttgtttttt tgtgttgctg cagttcccaa     5585 acttgccgag ttgccgactt gccgtgttga attgttatat atgttaaaag cctaaaatat    5645 atcctttcag aattgagatg gattgttgta actatcaggt ttttttttatt gagaatttta    5705 gatcaattag ttatcttgta attttttatt cttttaata caatactccc tccatcccaa     5765 tagcaaggtc cccttgctat tgggcacggg tattaaggag gaggattatt ataatgaaaa    5825 ttaatataaa gtaagtggat tccactttat taaggaatat tataatcaaa agtaatataa    5885 agtaagtgga ttccacttta attaggacac taattatttt ctttttttggt atgagacttt   5945 gctattggga catcccaaaa aggcaaaaga gaccttgcta ttaggacggt ggacgtgctg     6005 ccgaggcacg caaattaatt tacctttcct cttctatact aactcgtagt agcggcgagt     6065 aaaggtcgaa ccctcaagga gcaattgaac tagatgtgct attagaaata aaataaacac     6125 aagtgagagg ggagttttg gtttcaattt aactaaaact aattatgaaa atgaaaaaac     6185 aaatataaaa cataaacagg tagacgaaat atgataaaga tagaattcta gttctcggtt    6245 cagttatcac ctttctccaa gtatttcatg aataatgcaa cgcctctttt catacaactt     6305 agaatcgatg tccaaaggtt aatatcaagc tttatttacc taattgtctc gtacgattag    6365 ttaactaaaa caagctcttt aattaactct actcaattag ataacctaga ataagctctc    6425 tagagcggcc gccaccgcgg tggagctcca gcttttgttc cctttagtga gggttaattg    6485 cgcgcttggc gtaatcatgg tcatagctgt ttcctgtgtg aaattgttat ccgctcacaa    6545 ttccacacaa catacgagcc ggaagcataa agtgtaaagc ctggggtgcc taatgagtga    6605 gctaactcac attaattgcg ttgcgctcac tgcccgcttt ccagtcggga aacctgtcgt    6665 gccagctgca ttaatgaatc ggccaacgcg cggggagagg cggtttgcgt attgggccgc    6725 tcttccgctt ccttggttac ttgactcgct gcgctcggcc gtcggctgcg gcgagcggta    6785 tcaagctcac tcaaaggcgg taataccggn tatccacaga atcagggat                6835

<210> SEQ ID NO 5
<211> LENGTH: 240
<212> TYPE: PRT
```

-continued

<213> ORGANISM: Perilla frutescens

<400> SEQUENCE: 5

| Met | Arg | Val | Leu | Ala | Tyr | Gly | Ala | Ser | Ala | Asp | Val | Asp | Glu | Tyr |
| 1 | | | | 5 | | | | | 10 | | | | | 15 |

| Leu | Arg | Met | Ser | Ala | Thr | Val | Thr | Arg | Asp | Ala | Val | Ile | His | Phe | Val |
| | | | 20 | | | | | 25 | | | | | 30 | | |

| Glu | Gly | Val | Ile | Ser | Cys | Phe | Ser | Asp | Thr | Tyr | Leu | Arg | Lys | Pro | Asn |
| | | | 35 | | | | | 40 | | | | | 45 | | |

| Gln | Gln | Asp | Leu | Ala | Arg | Leu | Leu | Tyr | Val | Gly | Gln | Arg | Gly | Phe |
| | 50 | | | | | 55 | | | | | 60 | | | |

| Pro | Gly | Met | Ile | Gly | Ser | Ile | Asp | Cys | Met | His | Trp | Glu | Trp | Thr | Asn |
| 65 | | | | | 70 | | | | | 75 | | | | | 80 |

| Cys | Pro | Asn | Ala | Trp | Ala | Gly | Gln | Phe | Thr | Gly | Arg | Ser | Gly | Lys | Ser |
| | | | | 85 | | | | | 90 | | | | | 95 | |

| Thr | Ile | Ile | Leu | Glu | Ala | Val | Ala | Ser | Tyr | Asp | Leu | Trp | Ile | Trp | His |
| | | | 100 | | | | | 105 | | | | | 110 | | |

| Ala | Phe | Phe | Gly | Thr | Ser | Gly | Ala | Cys | Asn | Asp | Ile | Asn | Val | Leu | His |
| | | | 115 | | | | | 120 | | | | | 125 | | |

| Gly | Ser | Pro | Ile | Phe | Ser | Asp | Val | Leu | Glu | Gly | Arg | Ala | Pro | His | Val |
| | 130 | | | | | 135 | | | | | 140 | | | | |

| Ser | Tyr | Ile | Val | Asn | Gly | Arg | Gln | Asn | Asp | Arg | Ala | Tyr | Tyr | Leu | Thr |
| 145 | | | | | 150 | | | | | 155 | | | | | 160 |

| Asp | Gly | Ile | Tyr | Pro | Ser | Trp | Ala | Ala | Phe | Val | Lys | Ser | Ile | Thr | Ser |
| | | | | 165 | | | | | 170 | | | | | 175 | |

| Pro | Met | Thr | Arg | Lys | Tyr | Lys | Leu | Phe | Val | Gln | His | Gln | Glu | Ala | Ala |
| | | | 180 | | | | | 185 | | | | | 190 | | |

| Arg | Lys | Asp | Val | Glu | Arg | Ala | Phe | Gly | Val | Leu | Gln | Ala | Arg | Phe | Ala |
| | | 195 | | | | | 200 | | | | | 205 | | | |

| Phe | Ile | Arg | Arg | Pro | Cys | Leu | Val | Trp | Asp | Lys | Val | Leu | Met | Gly | Lys |
| | 210 | | | | | 215 | | | | | 220 | | | | |

| Ile | Met | Met | Ala | Cys | Ile | Ile | His | Asn | Met | Ile | Val | Glu | Asp | Glu |
| 225 | | | | | 230 | | | | | 235 | | | | | 240 |

<210> SEQ ID NO 6
<211> LENGTH: 448
<212> TYPE: PRT
<213> ORGANISM: Perilla frutescens

<400> SEQUENCE: 6

| Met | Thr | Thr | Thr | Val | Ile | Glu | Thr | Cys | Arg | Val | Gly | Pro | Pro | Asp |
| 1 | | | | 5 | | | | | 10 | | | | | 15 |

| Ser | Val | Ala | Glu | Gln | Ser | Leu | Pro | Leu | Thr | Phe | Phe | Asp | Met | Thr | Trp |
| | | | 20 | | | | | 25 | | | | | 30 | | |

| Leu | His | Phe | His | Pro | Met | Leu | Gln | Leu | Leu | Phe | Tyr | Glu | Phe | Pro | Cys |
| | | | 35 | | | | | 40 | | | | | 45 | | |

| Ser | Lys | Gln | His | Phe | Ser | Glu | Ser | Ile | Ile | Pro | Lys | Leu | Lys | Gln | Ser |
| | 50 | | | | | 55 | | | | | 60 | | | | |

| Leu | Ser | Lys | Thr | Leu | Ile | His | Phe | Phe | Pro | Leu | Ser | Cys | Asn | Leu | Ile |
| 65 | | | | | 70 | | | | | 75 | | | | | 80 |

| Tyr | Pro | Ser | Ser | Pro | Glu | Lys | Met | Pro | Glu | Phe | Arg | Tyr | Leu | Ser | Gly |
| | | | | 85 | | | | | 90 | | | | | 95 | |

| Asp | Ser | Val | Ser | Phe | Thr | Ile | Ala | Glu | Ser | Ser | Asp | Phe | Asp | Asp |
| | | | 100 | | | | | 105 | | | | | 110 | | |

| Leu | Val | Gly | Asn | Arg | Ala | Glu | Ser | Pro | Val | Arg | Leu | Tyr | Asn | Phe | Val |

```
              115                 120                 125
    Pro Lys Leu Pro Gln Ile Val Glu Glu Ser Asp Arg Lys Leu Phe Gln
        130                 135                 140

Val Phe Ala Val Gln Val Thr Leu Phe Pro Gly Arg Gly Val Gly Ile
    145                 150                 155                 160

Gly Ile Ala Thr His Thr Val Ser Asp Ala Pro Ser Phe Leu Ala
                    165                 170                 175

Phe Ile Thr Ala Trp Ala Trp Met Ser Lys His Ile Glu Asp Glu Asp
                180                 185                 190

Glu Glu Phe Lys Ser Leu Pro Val Phe Asp Arg Ser Val Ile Lys Tyr
                195                 200                 205

Pro Thr Lys Phe Asp Ser Ile Tyr Trp Lys Lys Ala Leu Lys Phe Pro
        210                 215                 220

Leu Gln Ser Arg His Pro Ser Leu Pro Thr Asp Arg Ile Arg Thr Thr
    225                 230                 235                 240

Phe Val Phe Thr Gln Ser Glu Ile Lys Lys Leu Lys Gly Ser Ile Gln
                    245                 250                 255

Ser Arg Val Pro Ser Leu Val His Leu Ser Ser Phe Val Ala Ile Ala
                260                 265                 270

Ala Tyr Met Trp Ala Gly Val Thr Lys Ser Leu Thr Ala Asp Glu Asp
                275                 280                 285

His Asp Asp Gly Asp Ala Phe Phe Leu Ile Pro Val Asp Leu Arg Pro
        290                 295                 300

Arg Leu Asp Pro Pro Val Pro Glu Asn Tyr Phe Gly Asn Cys Leu Ser
    305                 310                 315                 320

Tyr Ala Leu Pro Arg Met Arg Arg Glu Leu Val Gly Glu Lys Gly
                    325                 330                 335

Val Phe Leu Ala Ala Glu Ala Ile Ala Glu Ile Lys Lys Arg Ile
                340                 345                 350

Asn Asp Lys Arg Ile Leu Glu Thr Val Glu Lys Trp Ser Leu Glu Ile
                355                 360                 365

Arg Glu Ala Leu Gln Lys Ser Tyr Phe Ser Val Ala Gly Ser Ser Lys
    370                 375                 380

Leu Asp Leu Tyr Gly Ala Asp Phe Gly Trp Gly Lys Ala Arg Lys Gln
    385                 390                 395                 400

Glu Ile Leu Ser Ile Asp Gly Glu Lys Tyr Ala Met Thr Leu Cys Lys
                    405                 410                 415

Ala Arg Asp Phe Glu Gly Gly Leu Glu Val Cys Leu Ser Leu Pro Lys
                420                 425                 430

Asp Lys Met Asp Ala Phe Ala Ala Tyr Phe Ser Ala Gly Ile Asn Gly
                435                 440                 445

<210> SEQ ID NO 7
<211> LENGTH: 27
<212> TYPE: DNA
<213> ORGANISM: Artificial
<220> FEATURE:
<223> OTHER INFORMATION: HindIII containing primer

<400> SEQUENCE: 7
aagcttaact attatgatcc cacagag                                     27

<210> SEQ ID NO 8
<211> LENGTH: 24
<212> TYPE: DNA
<213> ORGANISM: Artificial
```

```
<220> FEATURE:
<223> OTHER INFORMATION: BamHI containing primer

<400> SEQUENCE: 8
ggatccggcg gtgttgaacg tagc                                           24

<210> SEQ ID NO 9
<211> LENGTH: 35
<212> TYPE: DNA
<213> ORGANISM: Artificial
<220> FEATURE:
<223> OTHER INFORMATION: Primer C1

<400> SEQUENCE: 9
gtacatattg tcgttagaac gcgtaatacg actca                               35

<210> SEQ ID NO 10
<211> LENGTH: 24
<212> TYPE: DNA
<213> ORGANISM: Artificial
<220> FEATURE:
<223> OTHER INFORMATION: Primer BP40-i5

<400> SEQUENCE: 10
aggtgcatga tcggaccata cttc                                           24

<210> SEQ ID NO 11
<211> LENGTH: 35
<212> TYPE: DNA
<213> ORGANISM: Artificial
<220> FEATURE:
<223> OTHER INFORMATION: Primer C2

<400> SEQUENCE: 11
cgttagaacg cgtaatacga ctcactatag ggaga                               35

<210> SEQ ID NO 12
<211> LENGTH: 25
<212> TYPE: DNA
<213> ORGANISM: Artificial
<220> FEATURE:
<223> OTHER INFORMATION: Primer BP40-i7

<400> SEQUENCE: 12
gaccatactt cttagcgagt ttggc                                          25

<210> SEQ ID NO 13
<211> LENGTH: 25
<212> TYPE: DNA
<213> ORGANISM: Artificial
<220> FEATURE:
<223> OTHER INFORMATION: Primer BP40pro-F

<400> SEQUENCE: 13
actcaaacaa gcatctcgcc atagg                                          25

<210> SEQ ID NO 14
<211> LENGTH: 2369
<212> TYPE: DNA
<213> ORGANISM: Viola x wittrockiana
<220> FEATURE:
<221> NAME/KEY: misc_feature
<223> OTHER INFORMATION: Plasmid pSFL614

<400> SEQUENCE: 14
actcaaacaa gcatctcgcc aatggttctc taaatttttct tctactctca tctcacgtgg   60
```

```
tttccgccaa tctgtctctg attacagcct tttcacatat gtcaaaggtt cagttagtgt    120
ttttgtcctt gtttatgtcg acgatataat cgttactggc aacaatctag atgccatttc    180
tgagactaaa caattcctcg caaattcatt ctctattaaa gatctcggca ctcttcgata    240
ttttcttgga atcgaagtat ctcgttctac gaaaggtatt ttcttatgtc aacgaaaata    300
cactctcgat attctctcag attctggtca ccttggatgt cgaccttctc catttcccat    360
ggagcaacat cttcatctac ttcctgatga tggtacacca ctcccgacc catccattta    420 tcgacgtctg gttggtcgac tactttactt gactgtcact cgtcctgata ttcaatatgc    480
agtgaatact cttagtcaat tcatgcaact tcctcgttcg acccatctcg atgcggcaaa    540
tcgagttctc cgatatctca aaggatcagt tggtaaagga atcctccttt cggccactag    600
tcctctttca cttgttggtt ttgctgattc tgactgggct ggttgtccaa ctactcgtcg    660
ttcaactact ggctacatta ccatgcttgg ttcaagtcct atctcttgga aaactaaaaa    720
gcaacccact gtctctcgat cttctgccga agccgaatat cgatcactcg ctgctctcac    780
ttcagagata cagtggcttc attatctact ctcggatctc ggttttcccc ctcaacaacc    840
gattaccgtt cattgtgaca accaagctgc tatacacatc gctaataatc cggttttcca    900
tgaacgaaca aagcacattg agctcgattg tcactttgtt cgtgaaaaaa ttatttctgg    960
tctcgtctcc accagttatt tgcgttcctc agatcaactt gctgatattt tcacaaaacc   1020
acttggtgca gatgcattta atcaccttat ttccaagttg ggcgtgatcg acatctctct   1080
cccggctcca acttgacggg gggtgttaaa cgtatacaag attttctaat cttgtatatt   1140
tgattttcta atatcttgta tatttgattt tctattatct tgtatttgaa cttttgtatt   1200
tccttagtat caggaaagtt agttgtagat attattttat atttcaaatc tgtatctaat   1260
acttgcctat ataaaggcca actaatcaat gaaatgaaca catcaatttt ctcaatttct   1320
cattctctgt tttcatatct attctctatt ttcacatttt ctgaaaagaa agatgcttga   1380
catgatcaga gacagttctt tcttcttcat actttcgtac taaacttctc ctggtccgca   1440
actaatcttc catcattttc ttgtgatctt cacttgagga tagtctctag aaaacggcac   1500
ggtcacgctg gataagtgtt taggatccct cgaagttgag ttgcatgaat ttgcgggta    1560 cgcaagtgac ttgactctta tcttggacgt cttatatgct cgaccaaatg ttggccaagt   1620
cgggatgctc gggttaagcc tctcttaggt caagtttatg agcgaacccc tttctttgag   1680
ggctctttat ttgccaactc gtctgccatt aaagttctat tagagctcta atgctgtgta   1740
tgtggctacc gatcacctc attctcagag gaatcctctt ttcgaatttc tggtactttg   1800
aaactagctg cttcaatttc agccactcga attaaacact aaaacagaac attgagagga   1860
acgggccctc ttcaaaatat agaaagaaac agataatgtc aaaagacaca tcaactaggt   1920
cgagatacct gctcacatgc atcacatcta accaactcga gtcggacgag aaatgagttc   1980
gtaactcgat gataataagg caaggtctaa aaccacatt cggttggtgg ttgtgttcat    2040
ggaccgatca cgtgccctaa cctaacccc gcatccatcc accaacagct agtcctcgcc    2100
gagtccccca aagttcctat ttatatcact aaagtcccct tttctcaaca tagacatgca   2160
aacacgagac aacatggcaa ttctagtcac cgacttcgtt gtcgcggcta taatttcttt   2220
gatcactcgg ttcttagttc gttctctttt caagaaacca acccgaccgc tccccccggg   2280
tcctctcggt tggcccttgg tgggcgccct ccctctccta ggcgccatgc ctcacgtcgc   2340
actagccaaa ctcgctaaga agtatggtc                                    2369
```

<210> SEQ ID NO 15
<211> LENGTH: 1102
<212> TYPE: DNA
<213> ORGANISM: Viola x wittrockiana
<220> FEATURE:
<221> NAME/KEY: misc_feature
<223> OTHER INFORMATION: BP40pro
<220> FEATURE:
<221> NAME/KEY: misc_feature
<222> LOCATION: (1)..(6)
<223> OTHER INFORMATION: HindIII
<220> FEATURE:
<221> NAME/KEY: misc_feature
<222> LOCATION: (1097)..(1102)
<223> OTHER INFORMATION: BamHI

<400> SEQUENCE: 15

```
aagcttgtga tcgacatctc tctcccggct ccaacttgac gggggggtgtt aaacgtatac    60
aagattttct aatcttgtat atttgatttt ctaatatctt gtatatttga ttttctatta   120
tcttgtattt gaacttttgt atttccttag tatcaggaaa gttagttgta gatattattt   180
tatatttcaa atctgtatct aatacttgcc tatataaagg ccaactaatc aatgaaatga   240
acacatcaat tttctcaatt tctcattctc tgttttcata tctattctct attttcacat   300
tttctgaaaa gaaagatgct tgacatgatc agagacagtt cttctcttct catactttcg   360
tactaaactt ctcctggtcc gcaactaatc ttccatcatt ttcttgtgat cttcacttga   420
ggatagtctc tagaaaacgg cacggtcacg ctggataagt gtttagctag cctcgaagtt   480
gagttgcatg aattttgcgg gtacgcaagt gacttgactc ttatcttgga cgtcttatat   540
gctcgaccaa atgttggcca agtcgggatg ctcgggttaa gcctctctta ggtcaagttt   600
atgagcgaac ccctttcttt gagggctctt tatttgccaa ctcgtctgcc attaaagttc   660
tattagagct ctaatgctgt gtatgtggct accgatcacc ttcattctca gaggaatcct   720
cttttcgaat ttctggtact ttgaaactag ctgcttcaat ttcagccact cgaattaaac   780
actaaaacag aacattgaga ggaacgggcc ctcttccaaa tatagaaaga aacagataat   840
gtcaaaagac acatcaacta ggtcgagata cctgctcaca tgcatcacat ctaaccaact   900
cgagtcggac gagaaatgag ttcgtaactc gatgataata aggcaaaggt ctaaaaccac   960
attcggttgg tggttgtgtt catggaccga tcacgtgccc taacctaacc cccgcatcca  1020
tccaccaaca gctagtcctc gccgagtccc ccaaagttcc tatttatatc actaaagtcc  1080
cttttttctca acatagggat cc                                          1102
```

<210> SEQ ID NO 16
<211> LENGTH: 25
<212> TYPE: DNA
<213> ORGANISM: Artificial
<220> FEATURE:
<223> OTHER INFORMATION: Primer BP40pro-HindIII-F

<400> SEQUENCE: 16

```
aagcttgtga tcgacatctc tctcc                                           25
```

<210> SEQ ID NO 17
<211> LENGTH: 21
<212> TYPE: DNA
<213> ORGANISM: Artificial
<220> FEATURE:
<223> OTHER INFORMATION: Primer BP40pro-NheI-R

<400> SEQUENCE: 17

-continued

```
cgaggctagc taaacactta t                                    21

<210> SEQ ID NO 18
<211> LENGTH: 20
<212> TYPE: DNA
<213> ORGANISM: Artificial
<220> FEATURE:
<223> OTHER INFORMATION: Primer BP40pro-NheI-F

<400> SEQUENCE: 18
tttagctagc ctcgaagttg                                      20

<210> SEQ ID NO 19
<211> LENGTH: 27
<212> TYPE: DNA
<213> ORGANISM: Artificial
<220> FEATURE:
<223> OTHER INFORMATION: Primer BP40pro-BamHI-R

<400> SEQUENCE: 19
ggatccctat gttgagaaaa agggact                              27

<210> SEQ ID NO 20
<211> LENGTH: 41
<212> TYPE: DNA
<213> ORGANISM: Artificial
<220> FEATURE:
<223> OTHER INFORMATION: Primer HAP gPf3ATpro long Fd

<400> SEQUENCE: 20
aagcttggcg cgccgtttaa caactatta tgatcccaca g               41

<210> SEQ ID NO 21
<211> LENGTH: 29
<212> TYPE: DNA
<213> ORGANISM: Artificial
<220> FEATURE:
<223> OTHER INFORMATION: Primer X-gPf3ATpro-RV

<400> SEQUENCE: 21
tctagaggcg gtgttgaacg tagctgtgg                            29

<210> SEQ ID NO 22
<211> LENGTH: 41
<212> TYPE: DNA
<213> ORGANISM: Artificial
<220> FEATURE:
<223> OTHER INFORMATION: Primer SSS-gPf3ATter-Fd

<400> SEQUENCE: 22
gagctcacta gtgtcgacta aatgtatgta attaaactaa t              41

<210> SEQ ID NO 23
<211> LENGTH: 43
<212> TYPE: DNA
<213> ORGANISM: Artificial
<220> FEATURE:
<223> OTHER INFORMATION: Primer ESS-gPf3ATter-Rv

<400> SEQUENCE: 23
gaattcaggc ctgcccgggc tatctttatc atatttcgtc tac            43

<210> SEQ ID NO 24
<211> LENGTH: 34
<212> TYPE: DNA
<213> ORGANISM: Artificial
```

<220> FEATURE:
<223> OTHER INFORMATION: Primer SpeISmaI-ADH-Fd

<400> SEQUENCE: 24
actagtcccg gggtctattt aactcagtat tcag                       34

<210> SEQ ID NO 25
<211> LENGTH: 29
<212> TYPE: DNA
<213> ORGANISM: Artificial
<220> FEATURE:
<223> OTHER INFORMATION: Primer SacI-BP40-Rv

<400> SEQUENCE: 25
gagctctcag gttgcgtacg ggtttgagg                             29

<210> SEQ ID NO 26
<211> LENGTH: 25
<212> TYPE: DNA
<213> ORGANISM: Artificial
<220> FEATURE:
<223> OTHER INFORMATION: primer RrF3H-F

<400> SEQUENCE: 26
aagcttctag ttagacaaaa agcta                                 25

<210> SEQ ID NO 27
<211> LENGTH: 25
<212> TYPE: DNA
<213> ORGANISM: Artificial
<220> FEATURE:
<223> OTHER INFORMATION: primer RrF3H

<400> SEQUENCE: 27
ggatcctctc ttgatatttc cgttc                                 25

<210> SEQ ID NO 28
<211> LENGTH: 33
<212> TYPE: DNA
<213> ORGANISM: Artificial
<220> FEATURE:
<223> OTHER INFORMATION: primer ADH-BP40-Fd

<400> SEQUENCE: 28
caagaaaaat aaatggcaat tctagtcacc gac                        33

<210> SEQ ID NO 29
<211> LENGTH: 20
<212> TYPE: DNA
<213> ORGANISM: Artificial
<220> FEATURE:
<223> OTHER INFORMATION: NcoI-BP40-Rv

<400> SEQUENCE: 29
ctcgagcgta cgtgagcatc                                       20

<210> SEQ ID NO 30
<211> LENGTH: 29
<212> TYPE: DNA
<213> ORGANISM: Artificial
<220> FEATURE:
<223> OTHER INFORMATION: primer BamHI-ADH-Fd

<400> SEQUENCE: 30
cgcggatccg tctatttaac tcagtattc                             29

```
<210> SEQ ID NO 31
<211> LENGTH: 35
<212> TYPE: DNA
<213> ORGANISM: Artificial
<220> FEATURE:
<223> OTHER INFORMATION: primer BP40-ADH-Rv

<400> SEQUENCE: 31
tagaattgcc atttattttt cttgatttcc ttcac                            35
```

METHOD FOR PRODUCING CHRYSANTHEMUM PLANT HAVING PETALS CONTAINING MODIFIED ANTHOCYANIN

CROSS REFERENCE TO RELATED APPLICATIONS

This application is a National Stage of International Application No. PCT/JP2010/053909 filed Mar. 9, 2010, and which claims benefit of Japanese Patent Application No. 2009-107055 filed Apr. 24, 2009, which are herein incorporated by reference in their entirety.

REFERENCE TO A SEQUENCE LISTING

A Sequence Listing containing SEQ ID NO: 1-31 is incorporated herein by reference.

TECHNICAL FIELD

The present invention relates to a method for controlling a flavonoid biosynthesis pathway in *chrysanthemum* plants using perilla-derived anthocyanin 3-acyltransferase (3AT) gene, a method for modifying anthocyanins, and a *chrysanthemum* plant transformed with the regulatory region thereof, progeny or vegetatively propagated product thereof, or a part or tissue thereof, and particularly a petal or cut flower thereof.

The present invention also relates to a transcriptional regulatory region derived from pansy flavonoid 3',5'-hydroxylase (to also be referred to as F3'5'H) gene #40, and to a use thereof.

BACKGROUND ART

The use of genetic recombination technology makes it possible to impart new traits to plants by expressing a useful gene in a target plant. Genetically modified plants produced in this manner have already been cultivated widely. Since regulation of gene expression is mainly controlled at the level of transcription, transcriptional regulation is the most important in terms of regulating the expression of genes. Namely, transcribing a gene at a suitable time, in a suitable tissue and at a suitable strength is important for producing an industrially useful genetically modified plant. In many cases, transcription is controlled by a DNA sequence on the 5'-side of a translated region. A region of DNA that determines the starting site of gene transcription and directly regulates the frequency thereof is referred to as a promoter. A promoter is located several tens of base pairs (bp) from the 5'-side of an initiation codon, and frequently contains a TATA box and the like. A cis element that binds various transcriptional regulatory factors is also present on the 5'-side, and the presence thereof serves to control the timing of transcription, the tissue in which transcription takes place and transcriptional strength. Transcriptional regulatory factors are classified into many families according to their amino acid sequence. For example, examples of well-known families of transcriptional regulatory factors include Myb transcriptional regulatory factors and bHLH (basic helix loop helix) regulatory factors. In actuality, the terms transcriptional regulatory factor and promoter are frequently used with the same meaning.

Anthocyanins, which compose the main components of flower color, are a class of secondary metabolites generically referred to as flavonoids. The color of anthocyanins is dependent on their structure. Namely, color becomes bluer as the number of hydroxyl groups on the B ring of anthocyanidins, which is the chromophore of anthocyanins, increases. In addition, as the number of aromatic acyl groups (such as coumaroyl group or caffeolyl group) that modify the anthocyanin increases (namely, the wavelength of maximum absorbance shifts to a longer wavelength), the color of the anthocyanin becomes bluer and the stability of the anthocyanin is known to increase (see Non-Patent Document 1).

Considerable research has been conducted on those enzymes and genes that encode those enzymes involved in the biosynthesis of anthocyanins (see, Non-Patent Document 1). For example, an enzyme gene that catalyzes a reaction by which an aromatic acyl group is transferred to anthocyanin is obtained from Japanese gentian, lavender and petunias (see Patent Document 1 and Patent Document 2). An enzyme gene involved in the synthesis of anthocyanin that accumulates in the leaves of perilla (malonylshisonin, 3-O-(6-0-(E)-p-coumaroyl-β-D-glucopyranosyl)-5-O-(6-O-malonyl-β-D-glucopyranosyl)-cyanidin) (see Non-Patent Document 2) has previously been reported in hydroxycinnamoyl CoA:anthocyanin 3-glucoside-aromatic acyl transferase (3AT) gene (or more simply referred to as "perilla anthocyanin 3-acyl transferase (3AT) gene") (see Patent Document 1). Moreover, knowledge has also been obtained regarding the transcriptional regulation (control) of biosynthetic genes of anthocyanins. Cis element sequences bound by Myb transcriptional regulatory factor and bHLH transcriptional regulatory factor are present in the transcriptional regulatory region located on the 5'-side of the initiation codons of these genes. Myb transcriptional regulatory factors and bHLH transcriptional regulatory factors are known to control synthesis of anthocyanins in petunias, maize and perilla (see Non-Patent Document 1).

Promoters (to also be referred to as transcriptional regulatory regions) responsible for gene transcription in plants consist of so-called constitutive promoters, which function in any tissue and at any time such as in the developmental stage, organ/tissue-specific promoters, which only function in specific organs and tissues, and time-specific promoters, which only express genes at a specific time in the developmental stage. Constitutive promoters are frequently used as promoters for expressing useful genes in genetically modified plants. Typical examples of constitutive promoters include cauliflower mosaic virus 35S promoter (to also be abbreviated as CaMV35S) and promoters constructed on the basis thereof (see Non-Patent Document 3), and Mac1 promoter (see Non-Patent Document 4). In plants, however, many genes are only expressed in specific tissues or organs or are only expressed at specific times. This suggests that tissue/organ-specific or time-specific expression of genes is necessary for plants. There are examples of genetic recombination of plants that utilize such tissue/organ-specific or time-specific transcriptional regulatory regions. For example, there are examples of protein being accumulated in seeds by using a seed-specific transcriptional regulatory region.

However, although plants produce flowers of various colors, there are few species capable of producing flowers of all colors due to genetic restrictions on that species. For example, there are no varieties of rose or carnation in nature that are capable of producing blue or purple flowers. This is because roses and carnations lack the F3'5'H gene required to synthesize the anthocyanindin, delphinidin, which is synthesized by many species that produce blue and purple flowers. These species can be made to produce blue flowers by transforming with the flavonoid 3',5'-hydroxylase gene of petunia or pansy, for example, which are species capable of producing blue and purple flowers. In the case of carnations, the transcriptional regulatory region of chalcone synthase gene derived from snapdragon or petunia is used to transcribe F3'5'H gene derived from a different species. Examples of plasmids containing the transcriptional regulatory region of chalcone synthase gene derived from snapdragon or petunia include plasmids pCGP485 and pCGP653 described in Patent Document 3, and examples of plasmids containing a constitutive transcriptional regulatory region include plasmid PCGP628 (containing a Mac1 promoter) and plasmid pSPB130 (containing a CaMV35S promoter to which is added EI2 enhancer) described in Patent Document 4.

However, it is difficult to predict how strongly such promoters function in recombinant plants to be able to generate a target phenotype. In addition, since repeatedly using the same promoter to express a plurality of foreign genes may cause gene silencing, it is thought that this should be avoided (see Non-Patent Document 5).

Thus, although several promoters have been used to alter flower color, a useful promoter corresponding to the target host plant and objective is still needed.

In particular, *chrysanthemum* plants (to also be simply referred to as *chrysanthemums*) account for about 30% of all wholesale flower sales throughout Japan (Summary of 2007 Flowering Plant Wholesale Market Survey Results, Ministry of Agriculture, Forestry and Fisheries), making these plants an important product when compared with roses accounting for roughly 9% and carnations accounting for roughly 7%. Although *chrysanthemums* come in flower colors including white, yellow, orange, red, pink and purplish red, there are no *chrysanthemums* that produce bluish flowers such as those having a purple or blue color. Thus, one objective of the breeding of bluish flowers is to stimulate new demand. *Chrysanthemum* flower color is expressed due to a combination of anthocyanins and carotenoids. Anthocyanins are able to express various colors due to differences in the structure of the anthocyanidin serving as the basic backbone, and differences in modification by sugars and organic acids. However, there are known to be two types of anthocyanins that govern *chrysanthemum* flower color in which cyanidin at position 3 is modified by glucose and malonic acid (cyanidin 3-O-(6"-O-monomalonyl-β-glucopyranoside and 3-O-(3",6"-O-dimalonyl-β-glucopyranoside) (see Non-Patent Document 6). In addition, these structures are comparatively simple (see FIG. 1). This causes the range of flower color attributable to anthocyanins in *chrysanthemums* to be extremely narrow.

As was previously described, although *chrysanthemums* are the most important flowering plant in Japan, since they are hexaploidal resulting in high ploidy and have a large genome size, in addition to having low transformation efficiency, since they are subject to the occurrence of silencing (deactivation) of transgenes, it is not easy to obtain genetically modified *chrysanthemums* capable of stable transgene expression. In *chrysanthemums* transfected with β-glucuronidase (GUS) gene coupled to CaMV35S promoter, the activity of the GUS gene is roughly one-tenth that of tobacco transformed with the same gene, and that activity has been reported to decrease in nearly all individuals after 12 months have elapsed following transformation (see Non-Patent Document 7). Although a promoter of gene that encodes a chlorophyll a/b-binding protein that favorably functions in *chrysanthemums* has been reported to have been obtained in order to stably express an exogenous gene in *chrysanthemums*, this promoter is not suitable for expressing genes in flower petals in which there is little chlorophyll present (see Non-Patent Document 8). In addition, when GUS gene coupled to tobacco elongation factor 1 (EF1α) promoter is introduced into *chrysanthemums*, GUS gene has been reported to be expressed in leaves and petals even after the passage of 20 months or more (see Non-Patent Document 9).

Moreover, there are also examples of flower life being prolonged by expressing a mutant ethylene receptor gene in *chrysanthemums* (see Non-Patent Document 10), flower form being changed by suppressing expression of *chrysanthemum* AGAMOUS gene (see Non-Patent Document 11), and expression of exogenous genes being increased in *chrysanthemums* by using a 5'-untranslated region of tobacco alcohol dehydrogenase (to also be referred to as tobacco ADH-5'UTR) (see Non-Patent Document 12).

On the other hand, although there have been examples of successful alteration of *chrysanthemum* flower color by genetic recombination, including a report of having changed pink flowers to white flowers by suppressing the chalcone synthase (CHS) gene by co-suppression (see Non-Patent Document 13), and a report of having changed white flowers to yellow flowers by suppressing carotenoid cleavage dioxygenase (CCD4a) by RNAi (see Non-Patent Document 14), all of these methods involve alteration of flower color by suppressing expression of endogenous genes, and there have been no successful examples of altering flower color by over-expression of exogenous genes as well as no examples of having realized a change in anthocyanin structure or an accompanying change in flower color.

Although attempts to alter flower color by over-expression of an exogenous gene have been reported that involve introducing a gene encoding F3'5'H, which is an enzyme required for synthesis of delphinidin (see Patent Document 5 and Non-Patent Document 15), the delphinidin produced due to the action of the introduced F3'5'H gene accumulates in ray petals, and there are no reports of the production of bluish *chrysanthemums*. In *chrysanthemums*, even if F3'5'H is expressed with CaMV35S promoter, production of delphinidin is not observed (see Non-Patent Document 15). In addition, expression of a gene expressed with CaMV35S promoter is unsuitable for stable expression, and for example, ends up dissipating accompanying growth of the *chrysanthemum* transformant (see Non-Patent Document 7). Potato Lhca3.St.1 promoter (see Non-Patent Document 16), *chrysanthemum* UEP1 promoter (see Non-Patent Document 17) and tobacco EF1α promoter (see Patent Document 6 and Non-Patent Document 9), for example, have been developed for use as promoters enabling efficient and stable expression of exogenous genes in the ray petals of *chrysanthemums*. However, there have been no reports describing alteration of *chrysanthemum* flower color by over-expression of an exogenous gene using these promoters. On the basis of the above, in order to produce *chrysanthemums* in which flower color has been altered by genetic recombination, it is necessary to establish a technology for controlling the expression of flavonoid biosynthesis genes, including the development of a promoter suitable for *chrysanthemums*.

PRIOR ART DOCUMENTS

Patent Documents

Patent Document 1: WO 96/25500

Patent Document 2: WO 01/72984

Patent Document 3: WO 94/28140

Patent Document 4: WO 05/17147

Patent Document 5: U.S. Pat. No. 5,948,955

Patent Document 6: Japanese Unexamined Patent Publication (Kokai) No. 2004-65096

Non-Patent Documents

Non-Patent Document 1: Plant J., 54, 737-749, 2008
Non-Patent Document 2: Agricultural and Biological Chemistry, 53, 797-800, 1989
Non-Patent Document 3: Plant Cell Physiology, 37, 49-59, 1996
Non-Patent Document 4: Plant Molecular Biology, 15, 373-381, 1990
Non-Patent Document 5: Annals of Botany, 79, 3-12, 1997
Non-Patent Document 6: Journal of Horticultural Science & Biotechnology, 81, 728-734, 2006
Non-Patent Document 7: Plant Biotechnology, 17, 241-245, 2000
Non-Patent Document 8: Breeding Science, 54, 51-58, 2004
Non-Patent Document 9: Japan Agricultural Research Quarterly, 39, 269-274, 2005
Non-Patent Document 10: Postharvest Biology and Technology, 37, 101-110, 2005
Non-Patent Document 11: Plant Biotechnology, 25, 55-59, 2008
Non-Patent Document 12: Plant Biotechnology, 25, 69-75, 2008
Non-Patent Document 13: Bio/Technology, 12, 268, 1994
Non-Patent Document 14: Plant Physiology, 142, 1193, 2006
Non-Patent Document 15: J. Plant Biol., 50, 626, 2007
Non-Patent Document 16: Mol. Breed., 8, 335, 2001
Non-Patent Document 17: Transgenic Res., 11, 437, 2002

SUMMARY OF THE INVENTION

Problems to be Solved by the Invention

An object of the present invention is to provide a method for controlling flavonoid biosynthesis in *chrysanthemum* plants by using a transcriptional regulatory region of perilla-derived anthocyanin 3-acyltransferase (3AT) gene, which is a useful promoter for altering flower color of *chrysanthemum* plants, a method for modifying anthocyanins, a method for producing a *chrysanthemum* plant containing modified anthocyanins in the petals thereof, and a *chrysanthemum* plant transformed with the transcriptional regulatory region, progeny or vegetative proliferation product thereof, or a part or tissue thereof, and particularly a petal or cut flower thereof.

The present invention also relates to a processed product that uses the aforementioned cut flower (cut flower processed product). Here, a cut flower processed product includes, but is not limited to, a pressed flower, preserved flower, dry flower or resin-embedded product obtained by using the cut flower.

An object of the present invention is to provide a useful promoter for altering flower color of *chrysanthemum* plants and non-*chrysanthemum* plants.

Means for Solving the Problems

As a result of conducting extensive studies and experiments to solve the aforementioned problems, the inventors of the present invention found that a transcriptional regulatory region of perilla-derived anthocyanin 3-acyltransferase (3AT) gene changes the structure of anthocyanin in *chrysanthemum* flower petals, and as a result thereof, is a useful promoter for altering flower color of *chrysanthemum* plants, and confirmed the usefulness thereof through experimentation, thereby leading to completion of the present invention.

The inventors of the present invention also found that a transcriptional regulatory region of pansy-derived F3'5'H gene is useful for altering flower color of *chrysanthemum* plants or plants other than *chrysanthemum* plants, thereby leading to completion of the present invention.

Namely, the present invention is as described below.

[1] A method for transcribing a nucleic acid in a *chrysanthemum* plant by genetic recombination technology using an expression vector or expression cassette containing a nucleic acid selected from the group consisting of:

(1) a nucleic acid comprising the nucleotide sequence indicated in SEQ ID NO. 1;

(2) a nucleic acid able to function as a transcriptional regulatory region of perilla anthocyanin 3-acyltransferase gene, and containing a nucleotide sequence in which the nucleotide sequence indicated in SEQ ID NO. 1 has been modified by addition, deletion and/or substitution of one or several nucleotides;

(3) a nucleic acid able to function as a transcriptional regulatory region of perilla anthocyanin 3-acyltransferase gene, and able to hybridize under high stringent conditions with a nucleic acid consisting of a nucleotide sequence complementary to the nucleotide sequence indicated in SEQ ID NO. 1; and, (4) a nucleic acid able to function as a transcriptional regulatory region of perilla anthocyanin 3-acyltransferase gene, and having sequence identity of at least 90% with the nucleotide sequence indicated in SEQ ID NO. 1.

[2] The method described in [1] above, wherein the method for transcribing the nucleic acid is a method for controlling flavonoid biosynthesis by transcribing a nucleic acid involved in flavonoid biosynthesis.

[3] The method described in [1] above, wherein the method for transcribing the nucleic acid is a method for modifying anthocyanins by transcribing a nucleic acid involved in anthocyanin modification.

[4] A method for producing a *chrysanthemum* plant containing an aromatic acylated anthocyanin in the petals thereof by expressing perilla anthocyanin 3-acyltransferase in a *chrysanthemum* plant using an expression vector or expression cassette containing a nucleic acid defined in [1] above.

[5] The method described in any of [1] to [4] above, wherein the expression vector or the expression cassette contains the nucleotide sequence indicated in SEQ ID NO. 2.

[6] A *chrysanthemum* plant, progeny thereof, or vegetatively propagated products, part or tissue thereof, transformed with the nucleic acid defined in [1] above or produced according to the method described in any of [1] to [5] above.

[7] The *chrysanthemum* plant, progeny thereof, or vegetatively propagated product, part or tissue thereof described in [6] above, containing an aromatic acylated anthocyanin.

[8] The *chrysanthemum* plant, progeny thereof, or vegetatively propagated product, part or tissue thereof described in [6] or [7] above, containing delphinidin.

[9] The *chrysanthemum* plant, progeny thereof, or vegetatively propagated product, part or tissue thereof described in any of [6] to [8] above, which is a cut flower.

[10] A cut flower processed product using the cut flower described in [9] above.

[11] A nucleic acid selected from the group consisting of:

(1) a nucleic acid comprising the nucleotide sequence indicated in SEQ ID NO. 15;

(2) a nucleic acid able to function as a transcriptional regulatory region of pansy F3'5'H gene, and containing a nucleotide sequence in which the nucleotide sequence indicated in SEQ ID NO. 15 has been modified by addition, deletion and/or substitution of one or several nucleotides;

(3) a nucleic acid able to function as a transcriptional regulatory region of pansy F3'5'H gene, and able to hybridize under high stringent conditions with a nucleic acid consisting of a nucleotide sequence complementary to the nucleotide sequence indicated in SEQ ID NO. 15; and, (4) a nucleic acid able to function as a transcriptional regulatory region of pansy F3'5'H gene, and having sequence identity of at least 90% with the nucleotide sequence indicated in SEQ ID NO. 15.

[12] A method for expressing a nucleic acid in a *chrysanthemum* plant or plant other than a *chrysanthemum* plant using an expression vector or expression cassette containing the nucleic acid described in [11] above.

[13] The method described in [12] above, wherein the method for expressing the nucleic acid is a method for controlling flavonoid biosynthesis by expressing a nucleic acid involved in flavonoid biosynthesis.

[14] The method described in [12] above, wherein the method for expressing the nucleic acid is a method for modifying anthocyanins by expressing a nucleic acid involved in anthocyanin modification.

[15] A *chrysanthemum* plant or non-*chrysanthemum* plant, progeny thereof, or vegetatively propagated products, part or tissue thereof, transformed with the nucleic acid defined in [11] above or produced according to the method described in any of [12] to [14] above.

[16] The *chrysanthemum* plant or non-*chrysanthemum* plant, progeny thereof, or vegetatively propagated products, part or tissue thereof described in [15] above, containing an aromatic acylated anthocyanin.

[17] The *chrysanthemum* plant or non-*chrysanthemum* plant, progeny thereof, or vegetative proliferation product, part or tissue thereof described in [15] or [16] above, containing delphinidin.

[18] The *chrysanthemum* plant or non-*chrysanthemum* plant, progeny thereof, or vegetatively propagated products, part or tissue thereof described in any of [15] to [17] above, which is a cut flower.

[19] A cut flower processed product using the cut flower described in [18] above.

Effects of the Invention

A transcriptional regulatory region thought to govern transcription of an enzyme gene in perilla leaves, namely a transcriptional regulatory region of perilla anthocyanin 3-acyltransferase, was determined to be able to function as a transcriptional regulatory region in the petals of a different species, *chrysanthemum*. Thus, transcription of an exogenous gene can be made to specifically occur in tissues such as flowers in which anthocyanins accumulate by using the transcriptional regulatory region of perilla anthocyanin 3-acyltransferase. Examples of the transcribed exogenous genes include, but are not limited to, genes relating to flower color and fragrance.

EMBODIMENTS OF THE INVENTION

Figure 1:
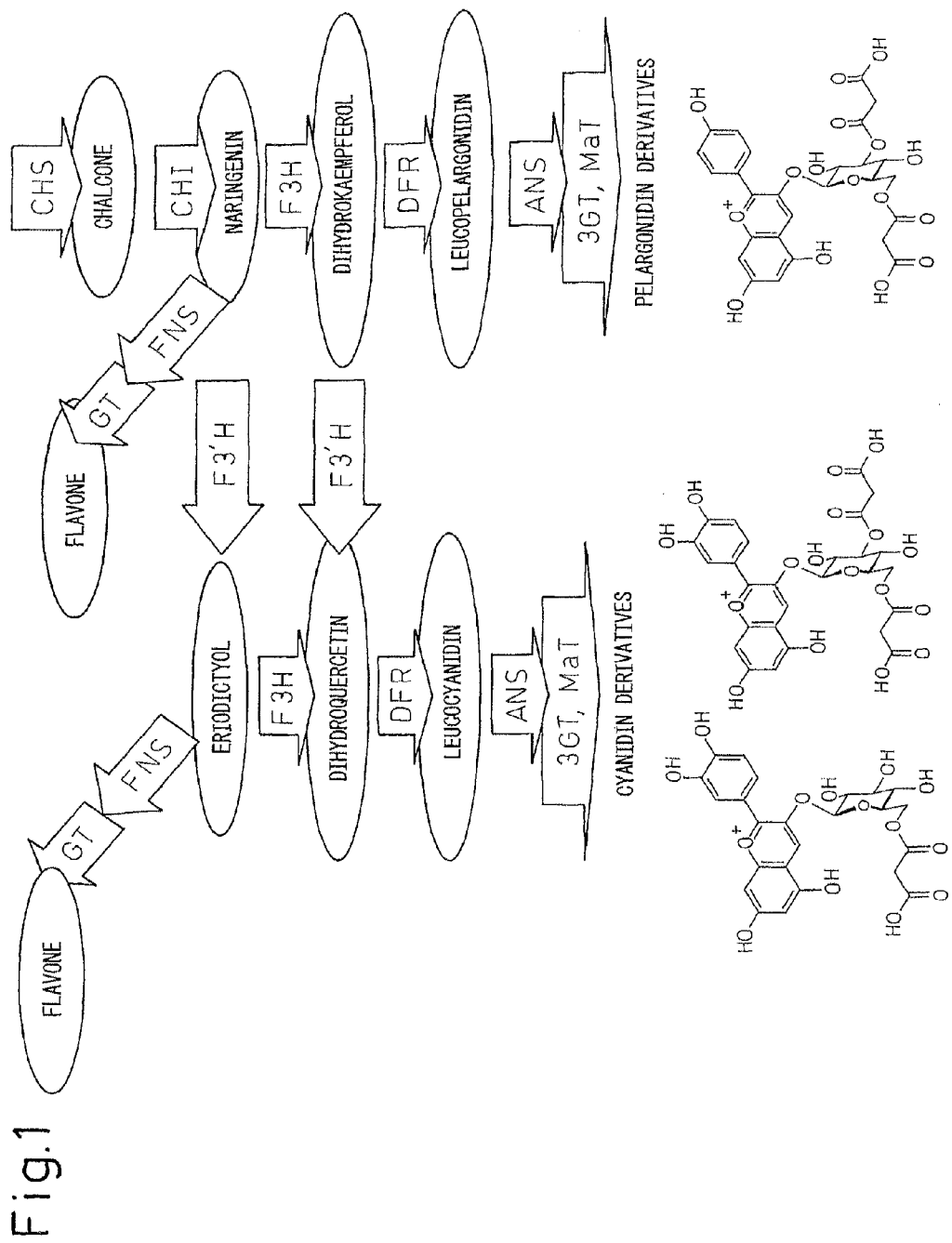
FIG. 1 is a schematic diagram of the flavonoid biosynthesis pathway in *chrysanthemums* and the structure of cyanidin 3-O-(6"-O-monomalonyl-β-glucopyranoside and cyanidin 3-O-(3",6"-O-dimalonyl-β-glucopyranoside.
Figure 2:
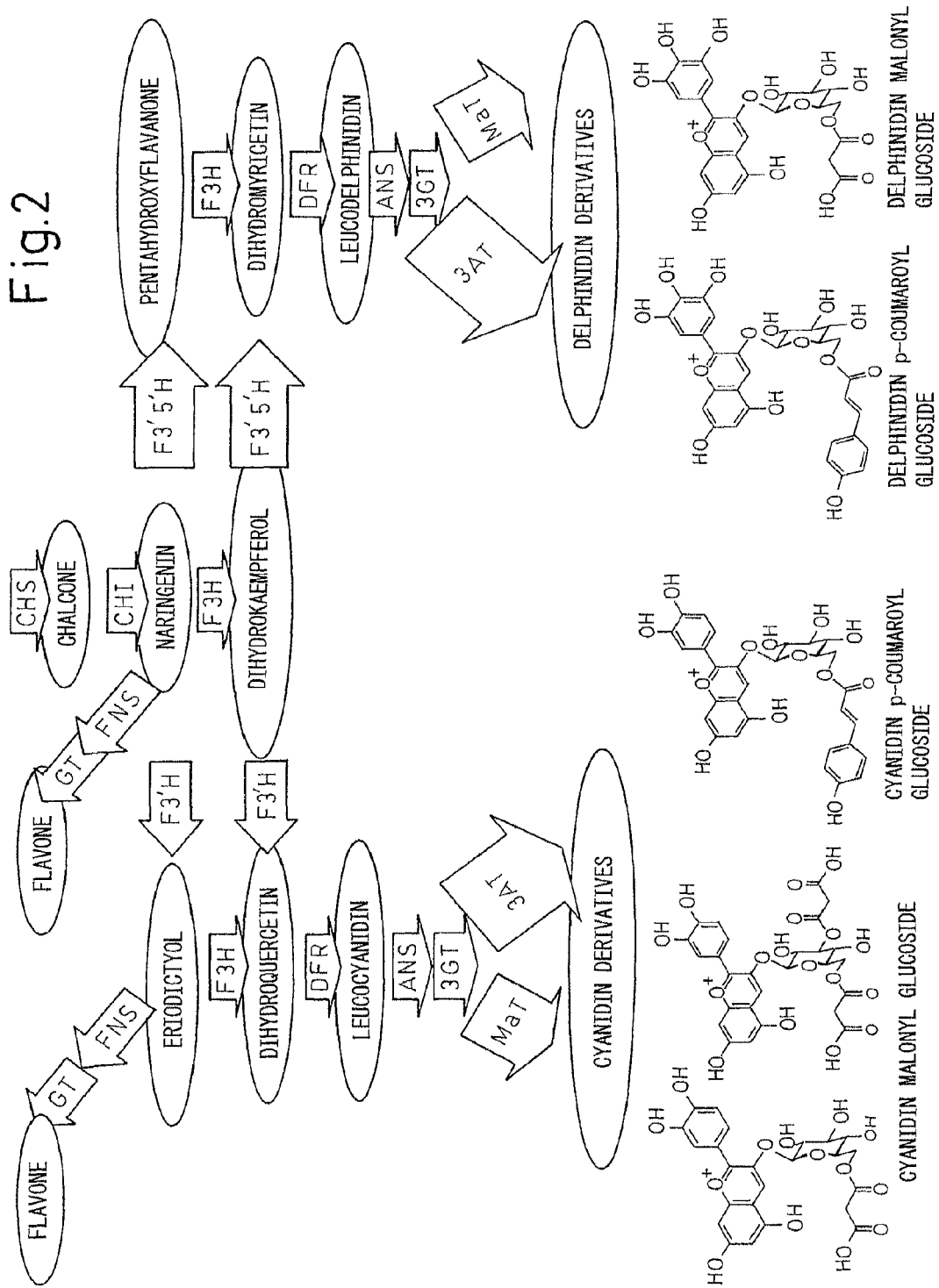
FIG. 2 indicates examples of flavonoid biosynthesis products of a transformed *chrysanthemum*.
Figure 3:
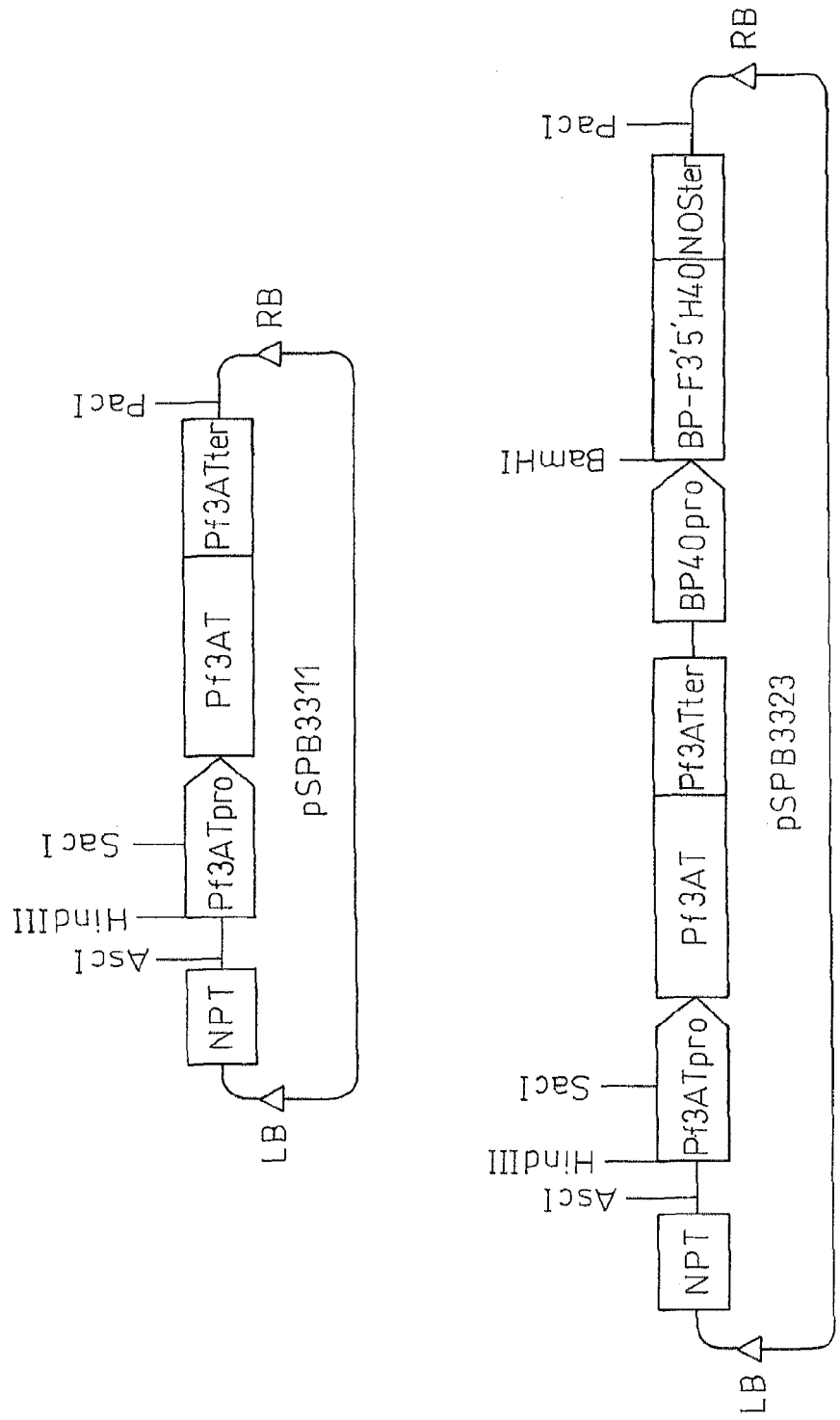
FIG. 3 is a schematic diagram of binary vectors pSPB3311 and pSPB3323 used to transfect perilla 3AT gene.

The present invention relates to a method for transcribing nucleic acid in a *chrysanthemum* plant, including transforming a *chrysanthemum* plant with a vector (see FIG. 3) containing an expression cassette that causes expression of a flavonoid biosynthesis enzyme gene such as 3AT or F3'5'H, by using the 5'-region of a gene (Pf3ATpro) that encodes perilla hydroxycinnamoyl CoA: anthocyanin 3-glucoside acyltransferase (Pf3AT) (also referred to in the present description as "transcriptional regulatory region of perilla anthocyanin 3-acyltransferase gene"), a method for controlling flavonoid biosynthesis by transcribing a nucleic acid involved in flavonoid biosynthesis, a method for modifying anthocyanins by transcribing a gene involved in anthocyanin modification, and a *chrysanthemum* plant produced according to the above method in which the anthocyanin composition of the flower petals thereof has been altered, and/or a *chrysanthemum* plant in which flower color has been altered, progeny or vegetatively propagated products thereof, or a part or tissue thereof, and particularly a petal or cut flower thereof.

Figure 7:
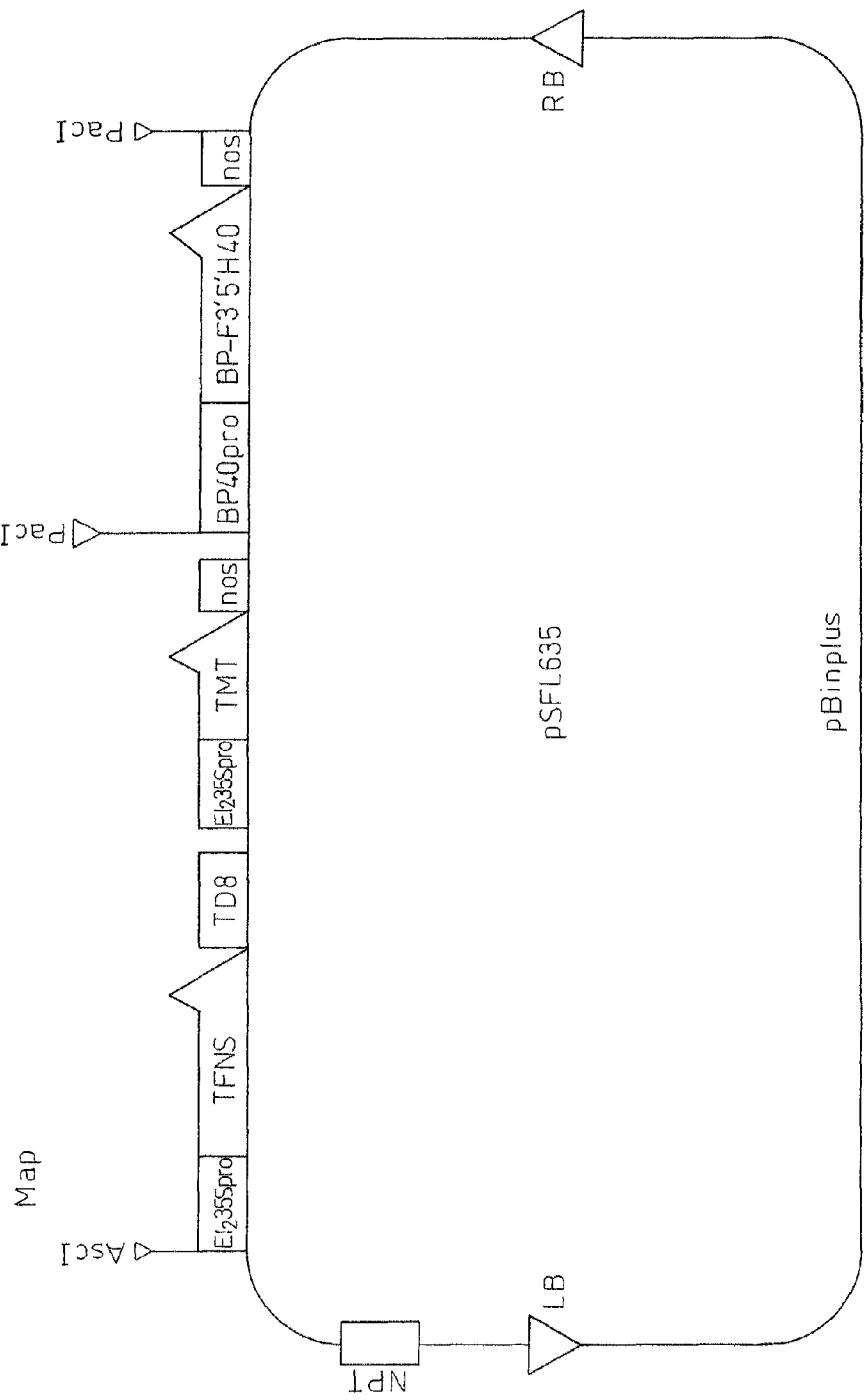
FIG. 7 is a schematic diagram of plasmid pSLF635.

The present invention relates to a method for transcribing nucleic acid in a *chrysanthemum* plant and a plant other than a *chrysanthemum*, including transforming a *chrysanthemum* plant and a plant other than *chrysanthemum* with a vector (see FIGS. 3 and 7) containing an expression cassette that causes expression of a flavonoid biosynthesis enzyme gene such as F3'5'H, by using the 5'-region of pansy F3'5'H gene (also referred to in the present description as "transcriptional regulatory region of pansy F3'5'H gene"), a method for controlling flavonoid biosynthesis by transcribing a nucleic acid involved in flavonoid biosynthesis, a method for modifying anthocyanins by transcribing a gene involved in anthocyanin modification, and a plant produced according to the above method in which the anthocyanin composition of the flower petals thereof has been altered, and/or a *chrysanthemum* plant or plant other than *chrysanthemum* in which flower color has been altered, progeny or vegetative proliferation product thereof, or a part or tissue thereof, and particularly a petal or cut flower thereof.

The present invention also relates to processed product that uses the aforementioned cut flower (cut flower processed product). Here, a cut flower processed product includes, but is not limited to, a pressed flower, preserved flower, dry flower or resin-embedded product obtained by using the cut flower.

In the present description, the "method for controlling flavonoid biosynthesis" refers to a method for controlling flavonoid biosynthesis by controlling expression of a gene that encodes a protein involved in flavonoid biosynthesis such as 3AT gene or F3'5'H gene. An example of the aforementioned anthocyanin 3-acyltransferase gene is perilla-derived anthocyanin 3-acyltransferase gene. In addition, an example of the F3'5'H gene is pansy-derived F3'5'H gene.

Figure 4:
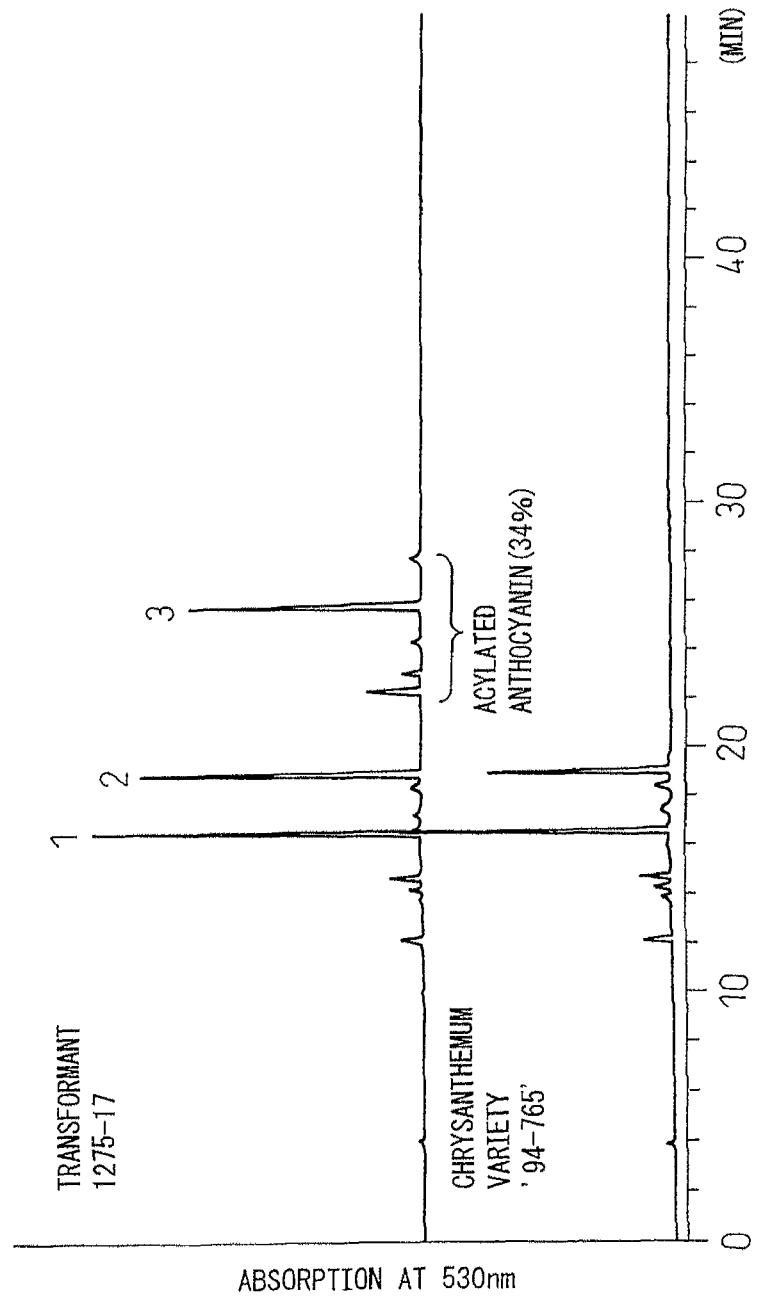
FIG. 4 indicates an HPLC chromatogram of a transformed *chrysanthemum* in which anthocyanin composition had been altered. The transformed *chrysanthemum* is a transformant 1275-17 containing 34% aromatic acylated anthocyanin, and the plasmid used is plasmid pSPB3311 (see FIG. 3). 1: Cyanidin 3-malonyl glucoside, 2: Cyanidin 3-dimalonyl glucoside, 3: cyanidin 3-aromatic acyl glucoside.
Figure 5:
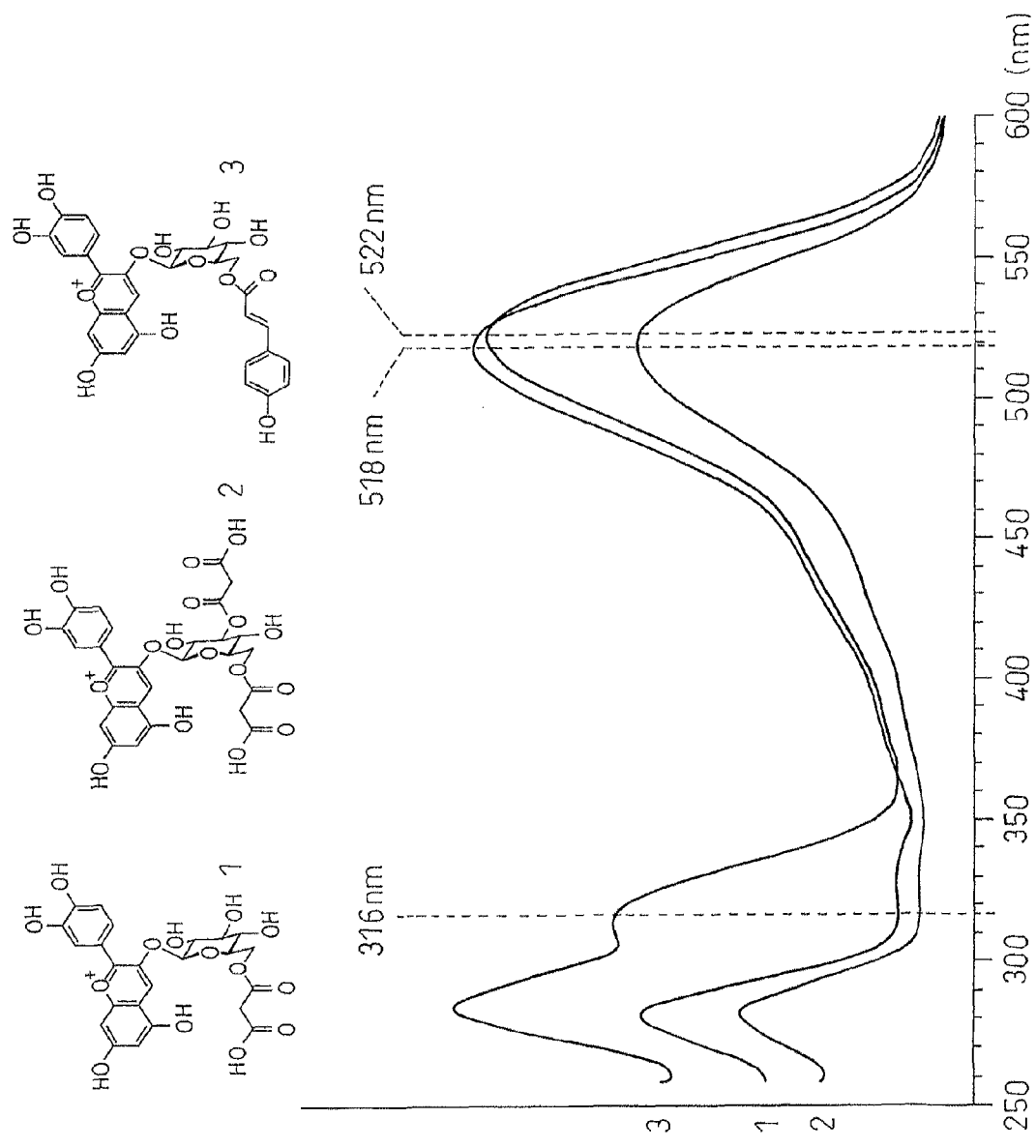
FIG. 5 indicates an absorption spectrum detected from the flower petals of a *chrysanthemum* transformant. Among the three absorption spectra, an absorption maximum was observed in the vicinity of 326 nm in anthocyanin modified with aromatic organic acid, while the absorption maximum of anthocyanin (roughly 5 nm from 518 nm to 522 nm) shifted towards a longer wavelength with respect to the absorption spectra of the malonylated forms (1,2).
Figure 6:
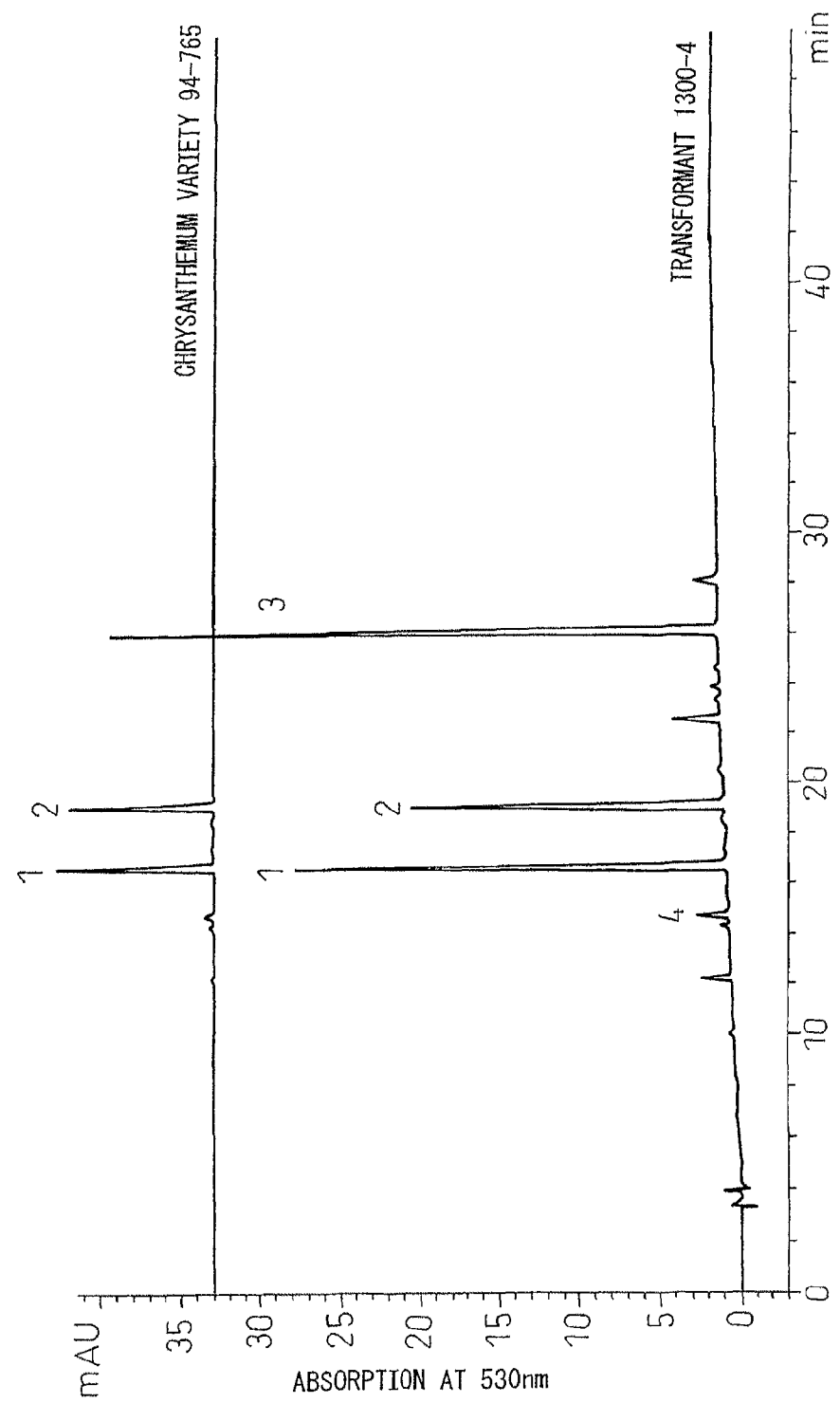
FIG. 6 indicates an HPLC chromatogram of a transformed *chrysanthemum* in which anthocyanin composition had been altered. The transformed *chrysanthemum* is a transformant 1300-4 containing 50% aromatic acylated anthocyanin and 0.8% delphinidin glycoside, and the plasmid used is plasmid pSPB3323 (see FIG. 3). 1: Cyanidin 3-malonyl glucoside, 2: Cyanidin 3-dimalonyl glucoside, 3: Cyanidin 3-aromatic acyl glucoside, 4: Delphinidin 3-malonyl glucoside.

According to the present invention, the absorption maxima of anthocyanins can be shifted to a longer wavelength making it possible to impart bluish color to an existing flower color by allowing an acyltransferase such as 3AT to function and transfer an aromatic acyl group to anthocyanins (see FIGS. 4, 5 and 6).

In addition, 34% to 50% of *chrysanthemum* anthocyanins can be aromatically acylated by expressing perilla 3AT gene with a Pf3AT promoter and Pf3AT terminator (see FIGS. 4 and 6), and by using this promoter to express various genes, an exogenous gene can be allowed to function efficiently and stably in ray petals of *chrysanthemum*. In addition, a glycoside of delphinidin, which serves as the basic backbone of blue anthocyanin, can be modified by an aromatic acyl group (see FIG. 6) making it possible to produce a blue *chrysanthemum* by simultaneously expressing F3'5'H gene and 3AT gene.

An example of a transcriptional regulatory region according to the present invention is a nucleic acid consisting of the nucleotide sequence indicated in SEQ ID NO. 1 or SEQ ID NO. 15. However, a promoter consisting of a nucleotide sequence in which one or several (1, 2, 3, 4, 5, 6, 7, 8, 9 or 10) nucleotides has been added, deleted and/or substituted in a nucleic acid consisting of the nucleotide sequence indicated in SEQ ID NO. 1 or SEQ ID NO. 15 is also thought to maintain activity similar to that of the original promoter. Thus, the transcriptional regulatory region according to the present invention can also be a nucleic acid consisting of a nucleotide sequence in which one or several nucleotides have been added, deleted and/or substituted in the nucleotide sequence indicated in SEQ ID NO. 1 or SEQ ID NO. 15 provided the nucleic acid is able to function as a transcriptional regulatory region in *chrysanthemum* flower petals or other plants.

The transcriptional regulatory region according to the present invention can also be a nucleic acid able to function as a transcriptional regulatory region of perilla anthocyanin 3-acyltransferase gene and able to hybridize under high stringent conditions with the nucleotide sequence indicated in SEQ ID NO. 1, or a nucleic acid able to function as a transcriptional regulatory region of perilla anthocyanin 3-acyltransferase gene and has sequence identity of at least 90% with the nucleotide sequence indicated in SEQ ID NO. 1.

The transcriptional regulatory region according to the present invention can also be a nucleic acid able to function as a transcriptional regulatory region of pansy F3'5'H gene and able to hybridize under highly stringent conditions with the nucleotide sequence indicated in SEQ ID NO. 15, or a nucleic acid able to function as a transcriptional regulatory region of pansy F3'5'H gene and has sequence identity of at least 90% with the nucleotide sequence indicated in SEQ ID NO. 15.

Examples of these nucleic acids include nucleic acids able to hybridize under high stringent conditions with the nucleotide sequence indicated in SEQ ID NO. 1 or SEQ ID NO. 15, and are consisting of nucleotide sequences having sequence identity with the nucleotide sequence indicated in SEQ ID NO. 1 or SEQ ID NO. 15 of preferably about 70% or more, more preferably about 80%, 81%, 82%, 83%, 84%, 85%, 86%, 87%, 88%, 89%, 90%, 91%, 92%, 93%, 94%, 95%, 96%, 97% or 98%, and most preferably about 99%.

Here, stringent conditions refer to hybridization conditions easily determined by a person with ordinary skill in the art that are determined empirically typically dependent on probe length, washing temperature and salt concentration. In general, the temperature for suitable annealing becomes higher the longer the probe, and the temperature becomes lower the shorter the probe. Hybridization is generally dependent on the ability of denatured DNA to re-anneal in the case a complementary strand is present in an environment at a temperature close to or below the melting temperature thereof.

More specifically, an example of low stringent conditions consists of washing and so forth in 0.1% SDS solution at 5×SSC under temperature conditions of 37° C. to 42° C. in the filter washing stage following hybridization. In addition, an example of high stringent conditions consists of washing and so forth in 0.1% SDS at 0.1×SSC and 65° C. in the washing stage. The use of more high stringent conditions makes it possible to obtain polynucleotides having higher homology or identity.

The transcriptional regulatory region according to the present invention is contained in an expression vector or expression cassette, and the expression vector or expression cassette contains a nucleotide sequence indicated for pansy F3'5'H gene described in, for example, SEQ ID NO. 2 or WO 04/020637.

The present invention also relates to a *chrysanthemum* plant or a plant other than *chrysanthemum*, progeny thereof, or part or tissue thereof, that has been transformed with the aforementioned transcriptional regulatory region (nucleic acid), and to a *chrysanthemum* plant or a plant other than *chrysanthemum*, progeny thereof, or vegetatively propagated products, part or tissue thereof, and particularly a flower petal or cut flower, containing aromatic acylated anthocyanins and/or delphinidin that is produced using the method according to the present invention.

In the present description, the term "*chrysanthemum* plant" (or simply "*chrysanthemum*") refers to a plant of family Asteraceae and genus *Chrysanthemum*. Examples thereof include *Dendranthema grandiflorum* Kitam, *Dendranthema*×*grandiflorum* cv.[standard], *Dendranthema*×*grandiflorum* cv.[large], *Dendranthema*×*grandiflorum* cv.[medium] and *Dendranthema*×*grandiflorum* cv.[floret], and an example of a typical species is *Chrysanthemum morifolium*. Although there are no particular limitations on the plant other than *chrysanthemum*, it can preferably be a rose.

EXAMPLES

The following provides a detailed explanation of the present invention through examples thereof.

Molecular biological techniques were carried out in accordance with Molecular Cloning (Sambrook and Russell, 2001) unless specifically indicated otherwise.

Example 1

Cloning of Perilla Anthocyanin 3-Acyl Transferase Chromosomal Gene

There are known to be red varieties of perilla in which anthocyanins accumulate in the leaves and green varieties in which they do not. Chromosomal DNA from the leaves of the former was prepared using a reported method (see Plant Mol.

Biol., December 1997, 35(6), 915-927). This chromosomal DNA was partially decomposed with Sau3AI (Toyobo), and a fraction containing a 10 kb to 15 kb DNA fragment was recovered using a sucrose density gradient method. This fragment was then inserted into the BamHI site of EMBL3 (Promega), a type of lambda phage vector, using a known method to prepare a chromosomal DNA library. The resulting library was screened using pSAT208 (see Plant Cell Physiol., April 2000, 41(4), 495-502), which is cDNA of anthocyanin 3-acyl transferase derived from perilla, as a probe. Screening of the library was in accordance with a previously reported method (see Plant Cell Physiol., July 1996, 37(5), 711-716). Plaques that hybridized with the probe were blunted and cultured, and DNA was prepared from the resulting phage.

Example 2

Nucleotide Sequence Determination of Perilla Anthocyanin 3-Acyltransferase Chromosomal Gene 10 µg of the DNA obtained above were digested with XbaI and isolated with 0.7% agarose gel followed by blotting onto Hybond-N (Amersham). When this film was hybridized in the same manner as previously described, a roughly 6.8 kb DNA fragment was found to hybridize with the probe. After digesting 20 µg of the same DNA with XbaI and isolating with 0.7% agarose gel, a roughly 6.8 kb DNA fragment was purified using GeneClean (Funakoshi) and coupled with pBluescript SKII-digested with XbaI. The resulting plasmid was designated pSPB513. The DNA sequence derived from perilla contained in this plasmid was determined by primer walking. The nucleotide sequence thereof is shown in SEQ ID NO. 4. This sequence is a region that demonstrates high homology with anthocyanin 3-acyl transferase cDNA in the form of pSAT208, the amino acid sequence (SEQ ID NO. 6) of protein encoded by this region was observed to demonstrate substitution of 19 amino acid residues and deletion of 2 amino acid residues in comparison with the amino acid sequence encoded by pSAT208, and there were no introns observed. In addition, the sequence of the region demonstrating high homology with pSAT208 contained a 3438 bp sequence upstream from ATG that was thought to be the start codon, and a 2052 bp sequence downstream from TAA that was thought to be the stop codon thereof. A different open reading frame (ORF, SEQ ID NO. 5), which was not anthocyanin 3-acyl transferase, was present in the aforementioned 3438 bp sequence. The following experiment was conducted to amplify the transcriptional regulatory region of perilla anthocyanin 3-acyl transferase gene, excluding this portion.

Example 3

Amplification of Transcriptional Regulatory Region of Perilla Anthocyanin 3-Acyl Transferase Gene PCR (holding for 1 minute at 95° C. followed by 25 cycles of a reaction consisting of 1 minute at 52° C., 2 minutes at 72° C. and 1 minute at 95° C.) was carried out using 1 ng of pSPB513 as template and two types of primers (5'-AAGCTTAACTATTATGATCCCACAGAG-3' (SEQ ID NO. 7, underline indicates HindIII recognition sequence) and 5'-GGATCCGGCGGTGTTGAACGTAGC-3' (SEQ ID NO. 8, underline indicates BamHI recognition sequence)). The amplified roughly 1.1 kb DNA fragment was digested with HindIII and BamHI.

The plasmid pSPB567 described in Patent Document 4 (in which pansy-derived flavonoid 3',5'-hydroxylase gene is coupled to the 3'-side of cauliflower mosaic 35S promoter to which has been added EI2 enhancer, and in which a nopaline synthase terminator is further coupled to the 3'-side thereof) was digested with PacI, and a DNA fragment containing pansy-derived F3'5'H gene was cloned into the PacI site of pBin+ (see Transgenic Research, 4, 288-290, 1995). A plasmid in which the cauliflower mosaic 35S promoter to which EI2 enhancer was added is present close to the AscI site of pBin+ in the resulting plasmid was designated pSPB575. This plasmid was then digested with HindIII and BamHI, and a DNA fragment obtained by digesting a roughly 1.1 kb DNA fragment containing the transcriptional regulatory region of the aforementioned perilla anthocyanin 3-acyl transferase with HindIII and BamHI was inserted therein. The resulting plasmid was designated pSFL205.

Plasmid pSFL205 was digested with HindIII and SacI, and a roughly 100 bp DNA fragment was recovered. This DNA fragment, a roughly 4 kb DNA fragment obtained by digesting pSPB513 with SacI and XbaI, and a plasmid pBin+ digested with HindIII and XbaI were coupled to obtain plasmid pSPB3311. This plasmid pSPB3311 is a binary vector that contains the nucleotide sequence indicated in SEQ ID NO. 2, and contains the transcriptional regulatory region of perilla anthocyanin 3-acyl transferase gene and an untranslated region of the 3'-side thereof.

Example 4

Construction of pSPB3323

The transcriptional regulatory region of pansy F3'5'H gene BP#40 (see WO 04/020637) was amplified as described below using the Takara LA PCR™ In Vitro Cloning Kit.

Chromosomal DNA was prepared from a pansy leaf using the DNA Easy Plant Kit (Qiagen). 3 µg of the chromosomal DNA were digested with restriction enzyme HindIII. The digested DNA was coupled with HindIII terminal DNA (included in the Takara LA PCR™ In Vitro Cloning Kit) by reacting for 40 minutes at 16° C. using Ligation High (Toyobo). After diluting 4 µl of the reaction mixture with 10 µl of water and denaturing the coupled DNA by treating for 10 minutes at 94° C., the reaction mixture was cooled in ice. 5 pmol of primer C1 (5'-GTACATATTGTCGTTAGAACGCG-TAATACGACTCA-3', SEQ ID NO. 9, included in the kit as a partial sequence of HindIII cassette sequence) and 5 pmol of primer BP40-i5 (5'-AGGTGCATGATCGGACCATACTTC-3', SEQ ID NO. 10, equivalent to a complementary strand of the translated region of BP#40) were then added followed by repeating 30 cycles of a reaction in 25 µl of the reaction mixture consisting of 20 seconds at 98° C. and 15 minutes at 68° C. in accordance with the kit protocol. The reaction mixture was then diluted 10-fold with water. After reacting for 5 minutes at 98° C. in 25 µl of a reaction mixture containing 5 pmol of primer C2 (5'-CGTTAGAACGCGTAATAC-GACTCACTATAGGGAGA-3', SEQ ID NO. 11, included in kit as partial sequence of HindIII cassette sequence) and 5 pmol of primer BP40-i7 (5'-GACCATACTTCTTAGC-GAGTTTGGC-3', SEQ ID NO. 12) using 0.5 µl of this dilution as template, 30 cycles of a reaction were repeated consisting of reacting for 20 seconds at 98° C. and 15 minutes at 68° C.

The resulting DNA fragment was inserted into plasmid pCR2.1 (Invitrogen). When the nucleotide sequence of the inserted DNA was determined, the sequence was observed to have locations that did not coincide with the cDNA nucleotide sequence of BP#40. This is thought to be due to the occurrence of an error during PCR. The following procedure was carried out for the purpose of amplifying an error-free sequence.

In order to amplify a roughly 2 kb 5'-untranslated region and a 200 bp translated region of BP#40, PCR was carried out in 25 μl of a reaction mixture using 200 ng of pansy chromosomal DNA as template and using 50 pmol of primer BP40-i7 (SEQ ID NO. 12) and 50 pmol of primer BP40 pro-F (5'-ACTCAAACAAGCATCTCGCCATAGG-3', SEQ ID NO. 13, sequence in 5'-untranslated region of BP#40 gene). After treating for 5 minutes at 98° C., a reaction consisting of 20 seconds at 98° C. and 15 minutes at 68° C. was repeated for 30 cycles. The amplified DNA fragment was inserted into pCR2.1. This DNA fragment contained a roughly 2.1 bp 5'-untranslated region and a 200 bp translated region. This plasmid was designated pSFL614. The nucleotide sequence of plasmid pSFL614 is shown in SEQ ID NO. 14.

The roughly 2.1 kb 5'-untranslated region (BP40pro, SEQ ID NO. 15) contained in pSFL614 was used to transcribe BP#40 gene. At this time, the BamHI site was changed to NehI. After using 1 ng of pSFL614 as template, adding 50 pmol of primer BP40pro-HindIII-F (5'-AAG CTT GTG ATC GAC ATC TCT CTC C-3', SEQ ID NO. 16), 50 pmol of primer BP40pro-NehI-R (5'-CGA GGC TAG CTA AAC ACT TAT-3', SEQ ID NO. 17), Ex-Taq DNA polymerase and holding for 5 minutes at 98° C. in 25 μl of the reaction mixture, a reaction consisting of 20 seconds at 98° C. and 15 minutes at 68° C. was repeated for 25 cycles. The amplified DNA fragment was cloned into pCR2.1. This sequence was determined to be free of errors attributable to PCR by confirming the nucleotide sequence thereof. This plasmid was then digested with HindIII and NheI to obtain a 470 bp DNA fragment. This DNA fragment was designated fragment A.

After using 1 ng of pSLF614 as template, adding 50 pmol of primer BP40pro-NehI-F (5'-TTT AGC TAG CCT CGA AGT TG-3', SEQ ID NO. 18), 50 pmol of primer BP40pro-BamHI-R (5'-GGA TCC CTA TGT TGA GAA AAA GGG ACT-3', SEQ ID NO. 19) and Ex-Taq DNA polymerase, and holding for 5 minutes at 98° C. in 25 μl of the reaction mixture, a reaction consisting of 20 seconds at 98° C. and 15 minutes at 68° C. was repeated for 25 cycles. The amplified DNA fragment was cloned into pCR2.1. This sequence was determined to be free of errors attributable to PCR by confirming the nucleotide sequence thereof. This plasmid was then digested with HindIII and NheI to obtain a 630 bp DNA fragment. This DNA fragment was designated fragment B.

The larger of the DNA fragments formed by digesting plasmid pSPB567 described in Patent Document 4 with HindIII and NheI was recovered, and coupled with the aforementioned fragment A and fragment B to obtain pSFL620.

After digesting pSFL620 with PacI, a roughly 3.2 kb DNA fragment was recovered. This DNA fragment was inserted into the PacI site of pBin+. The resulting plasmid was designated pSPB3317. A fragment obtained by digesting the aforementioned pSPB3311 with AscI and XbaI was transfected to the AscI and XbaI sites of pSPB3317, and the resulting plasmid was designated pSPB3323.

Example 5

Expression of Perilla Anthocyanin 3-Acyltranferase Chromosomal Gene in *Chrysanthemum*

The pSPB3311 prepared in Example 3 was transfected into *Agrobacterium* and *chrysanthemum* variety 94-765 8Seikouen, not soled) was transformed according to a known method using this *Agrobacterium*. Although *chrysanthemum* transformation is described in Non-Patent Document 8, the transformation method is not limited thereto. Six transformed lines were acquired. A ray petals thereof was frozen and then crushed followed by extracting 50 mg to 100 mg of the crushed petal with 500 μL of 50% aqueous acetic acid and filtering with a 0.45 μm filter. The anthocyanins contained in this extract was diluted five-fold with distilled water and used as an analysis sample that was analyzed under the following conditions using high-performance liquid chromatography. An Inertsil ODS-2 column (particle diameter: 5 μm, 4.6×25 mm, GL Sciences) was used for the column, the flow rate was 0.8 ml/min, the mobile phase contained 1.5% phosphoric acid, and isocratic elution was carried out for 40 minutes using a linear concentration gradient from 4% acetic acid and 5% acetonitrile to 20% acetic acid and 25% acetonitrile, followed by eluting for 10 minutes with 25% acetonitrile containing 1.5% phosphoric acid and 20% acetic acid. Detection was carried out using the Agilent 1100 Series Diode Array Detector (GL Sciences) over a wavelength range of 250 nm to 600 nm, and the content ratio of each anthocyanidin was determined according to the area of optical absorbance at 530 nm.

Among the anthocyanins in the transformants consisting of analyzed lines 1275-13, 1275-14, 1275-15 and 1275-17, 23%, 1%, 17% and 34%, respectively, had retention times of 20 minutes or longer, and these anthocyanins were suggested to have been modified by aromatic acyl groups. The absorbance maxima of the anthocyanins that eluted at retention times of 20 minutes or longer shifted to a longer wavelength, and existing flower color was able to be made bluish as a result of the aforementioned transformation. On the other hand, none of the anthocyanins present in flower petals of the original *chrysanthemum* variety 94-765 demonstrated retention times of 20 minutes or more.

Anthocyanins of transformed *chrysanthemum* 1275-17 were analyzed by LC-FT-ICR-MS (J. Japan Soc. Hort. Sci., 77, 94-102 (2008) and Plant J., 54, 949-962). The use of this technique makes it possible to precisely measure the mass spectra of the anthocyanins and obtain MS/MS spectra by tandem mass spectrometry. A peak corresponding to a compound equivalent to cyanidin (coumaroyl) glucoside (detected m/z: 595.146259), which is not detected in the host, was detected in *chrysanthemum* transformant 1275-17, and only the fragment m/z 287.1 corresponding to cyanidin was detected among the MS/MS fragments.

On the basis of the above results, the transcriptional regulatory region of 3AT of a different species in the form of perilla was determined to function in a *chrysanthemum* plant, and this perilla 3AT was determined to function in *chrysanthemum* and change anthocyanin structure and flower color. In addition, according to the present invention, the absorption maxima of anthocyanins was determined to shift to a longer wavelength as a result of allowing an acyltransferase such as 3AT to function and transfer an aromatic acyl group to anthocyanin (see FIGS. 4, 5 and 6).

Example 6

Expression of Perilla Anthocyanin 3-Acyl Transferase Chromosomal Gene and Pansy F3'5'H Gene in *Chrysanthemum*

The pSPB3323 prepared in Example 4 was transfected into *Agrobacterium* and *chrysanthemum* variety 94-765 (Seikoen, not sold) was transformed according to a known method using this *Agrobacterium*. Six transformed lines were acquired. The anthocyanins contained in the flower petals were analyzed using high-performance liquid chromatography according to the method described in Example 5.

20%, 2% and 50% of the anthocyanins in transformants in the form of analyzed lines 1300-2, 1300-3 and 1300-4, respectively, had retention times of 20 minutes or longer, and these anthocyanins were suggested to have been modified by aromatic acyl groups. None of the host anthocyanins demonstrated retention times of 20 minutes or longer. On the basis of these findings, it was clear that transcriptional regulatory region of 3AT of a different species in the form of perilla had functioned in a *chrysanthemum* plant, and that anthocyanin structure and flower color were altered as a result of this perilla 3AT having functioned in *chrysanthemum*. Thus, the use of the transcriptional regulatory region of perilla anthocyanin 3-acyltransferase gene to express various genes enables exogenous genes to function both efficiently and stably in lingulate flower petals of *chrysanthemum*.

In addition, anthocyanidins extracted according to the method described below were analyzed. Ray petals were frozen and then crushed followed by extracting 50 mg to 100 mg of the crushed petal with 500 μL of 1% hydrogen chloride-methanol, adding 500 μL of 4 N hydrochloric acid (HCl) to this extract and mixing, and hydrolyzing for 1 hour at 100° C. After cooling the solution following hydrolysis, 1 ml of 0.05 M trifluoroacetic acid (TFA) was added and mixed therein. Next, this solution was added to Sep-Pak C18 (Millipore) to adsorb the hydrolysis product. The Sep-Pak C18 was preliminarily washed with 80% acetonitrile (MeCN) and equilibrated with 0.05 M TFA. After washing the hydrolysis product adsorbed to the Sep-Pak C18 with 0.05 M TFA, the hydrolysis product was further washed with 20% MeCN and 0.05 M TFA followed by eluting the hydrolysis product with 80% MeCN and 0.05 M TFA to obtain an analysis sample.

The analysis sample was analyzed under the following conditions using high-performance liquid chromatography. An Inertsil ODS-2 column (particle diameter: particle size: 5 μm, 4.6×25 mm, GL Sciences) was used for the column, the flow rate was 0.8 ml/min, the mobile phase contained 1.5% phosphoric acid, and isocratic elution was carried out for 20 minutes using a linear concentration gradient from 5% acetic acid and 6.25% acetonitrile to 20% acetic acid and 25% acetonitrile, followed by eluting for 5 minutes with 25% acetonitrile containing 1.5% phosphoric acid and 20% acetic acid. Detection was carried out using the Agilent 1100 Series Diode Array Detector (GL Sciences) over a wavelength region of 250 nm to 600 nm, and the abundance ratios of each of the anthocyanidins was determined according to the area of optical absorbance at 530 nm.

As a result of analysis, delphinidin was detected at ratios of 0.9%, 0.8%, 1.4% and 0.6% of the total amount of anthocyanidins in transformants consisting of analyzed lines 1300-3, 1300-4, 1300-5 and 1300-6, respectively. This suggests that BP#40 transcriptional regulatory region of pansy governs transcription of BP#40. Delphinidin-type anthocyanins modified with aromatic acyl groups were suggested to also be contained in lines 1300-3 and 1300-4 in which delphinidin and anthocyanins that were suggested to have been modified by aromatic acyl groups were detected. In this manner, a glycoside of delphinidin, which serves as the basic backbone of blue anthocyanin, can be modified by an aromatic acyl group making it possible to produce a blue *chrysanthemum* by simultaneously expressing F3'5'H gene and 3AT gene.

Example 7

Production of pBI121-Perilla 3ATpro::ADHNF-Pansy F3'5'H#40::Perilla 3ATter

A roughly 1.1 kbp promoter region (Pf3ATpro) of perilla anthocyanin 3-acyltransferase gene (Pf3AT) was amplified by carrying out PCR with Prime Star DNA polymerase (Takara) using the plasmid pSPB3311 obtained in Example 3 as template, and using HAP gPf3ATpro long Fd (5'-AAGCT-TGGCGCGCCGTTTAAACAACTATTAT-GATCCCACAG-3', SEQ ID NO. 20) and X-gPf3ATpro-Rv (5'-TCTAGAGGCGGTGTTGAACGTAGCTGTGG-3', SEQ ID NO. 21) as primers. The resulting PCR product was cloned into pCR-BluntII-TOPO (Invitrogen) and the resulting plasmid was designated pCR-Pf3ATpro.

Next, a roughly 1.5 kbp 3'-untranslated region (Pf3ATter) of perilla anthocyanin 3-acyltransferase gene was amplified by PCR with Prime Star DNA polymerase (Takara) using pSPB3311 as template, and using SSS-gPf3ATter-FD (5'-GAGCTCACTAGTGTCGACTAAATGTATG-TAATTAAACTAAT-3', SEQ ID NO. 22) and ESS-gPf3ATter-Rv (5'-GAATTCAGGCCTGCCCG-GGCTATCTTTATCATATTTCGTCTAC-3', SEQ ID NO. 23) as primers. The PCR product was cloned into pCRBluntII-TOPO (Invitrogen) and the resulting plasmid was designated pCR-Pf3ATter.

A Pf3ATter DNA fragment obtained by digesting pCR-Pf3ATter with SacI and EcoRI was inserted into the SacI and EcoRI sites of pBI121-ADHNF. Next, the resulting plasmid was digested with HindIII and XbaI and coupled with a pF3ATpro DNA fragment obtained by digesting pCR-Pf3ATpro with HindIII and XbaI, and the resulting binary vector was designated pBI121-Pf3ATp-GUS-Pf3ATt.

A *Rosa tugosa* chromosomal DNA library was prepared in the manner described below using the λBlueSTAR™ Xho I Half-Site Arms Kit (Novagen, http://www.merckbiosciences.com/product/69242). Chromosomal DNA was prepared from a young leaf of *Rosa tugosa* using Nucleon Phytopure™ (Tepnel Life Sciences). Roughly 100 μg of chromosomal DNA were digested with restrictase Sau3AI.

This DNA fragment was then partially filled in with DNA polymerase I Klenow fragment (Toyobo) in the presence of dGTP and dATP, and fractionated by sucrose density gradient centrifugation. DNA of about 13 kb was recovered and concentrated by ethanol precipitation. Roughly 180 ng of DNA were ligated for 15 hours at 4° C. with 1 μL of the λBlue-STAR™ Xho I Half-Site Arms Kit, followed by carrying out in vitro packaging to obtain a chromosome library.

This *Rosa tugosa* chromosomal DNA library was screened with torenia flavanone 3-hydroxylase (F3H) cDNA (NCBI No. AB211958) to obtain plaques indicating signals. One of these plaques was converted to a plasmid by carrying out in vivo splicing using the method recommended by the manufacturer (Novagen). This was then digested with restriction enzyme SpeI to recover a 2.6 kb DNA fragment, and plasmid pSPB804 was obtained by sub-cloning this DNA fragment to the SpeI site of pBluescript SKIT—(Stratagene). This plasmid had a nucleotide sequence that demonstrates homology with F3H.

In order to amplify the 5'-untranslated region of F3H, PCR was carried out in 50 μl of a reaction mixture by using 1 ng of pSPB804 as template, using primer RrF3H-F (5'-AAGCT-TCTAGTTAGACAAAAAGCTA-3', SEQ ID NO. 26) and primer RrF3H (5'-GGATCCTCTCTTGATATTTCCGTTC-3', SEQ ID NO. 27), and using Ex-Taq DNA Polymerase (Takara). PCR reaction conditions consisted of reacting for 5 minutes at 94° C., repeating 30 cycles of reaction of which one cycle consisted of 30 seconds at 94° C., 30 seconds at 50° C. and 30 seconds at 72° C., and finally holding for 7 minutes at 72° C. The resulting DNA fragment was inserted into pCR-TOPO (Invitrogen) to obtain plasmid pSPB811. A roughly 2.1 kb F3H 5'-untranslated region was able to be recovered from this plasmid using HindIII and BamHI.

Plasmid pSFL814 (containing *R. rugosa* F3H 5':BFP3'5'#40:nos 3') was obtained by substituting the promoter portion of pSPB567 described in Patent Document 4 (plasmid pUC containing CaMV35S promoter to which has been added EI2 enhancer, pansy F3'5'HBP40 and nopaline synthase terminator) with the roughly 1.2 kb 5'-untranslated region of F3H using HindIII and BamHI.

A DNA fragment amplified by PCR using pSLF814 as template and using ADH-BP40-Fd (5'-CAA-GAAAAATAAATGGCAATTCTAGTCACCGAC-3', SEQ ID NO. 28) and NcoI-BP40-Rv (5'-CTCGAGCGTACGT-GAGCATC-3', SEQ ID NO. 29) as primers, and a DNA fragment amplified by PCT using pB1221 ADH-221 as template and using BamHI-ADH-Fd (5'-CGCGGATCCGTC-TATTTAACTCAGTATTC-3', SEQ ID NO. 30) and BP40-ADH-Rv (5'-TAGAATTGCCATTTATTTTTCTTGATTTCCTTCAC-3', SEQ ID NO. 31) as primers were mixed, and a DNA fragment in which tobacco ADH-5'UTR 94 bp was directly coupled to the start codon of pansy F3'5'H#40 was obtained by PCR using this mixture of DNA fragments as template and using BamHI-ADH-Fd and NcoI-BP40-Rv as primers.

After TA-cloning this DNA fragment to pCR2.1, a roughly 600 bp DNA fragment obtained by digesting with BamHI and NcoI and a binary vector fragment obtained by digesting pSFL814 with BamHI and NcoI were ligated to obtain pBinPLUS Rugosa rose F3Hpro:ADHNF-pansy-F3'5'H#40::NOSter.

An ADHNF-pansy-F3'5'H#40 DNA fragment was amplified by PCR using the pBinPLUS *Rosa rugosa* F3Hpro: ADHNF-pansy-F3'5'H#40:: NOSter as template, using SpeISmaI-ADH-Fd (5'-ACTAGTCCCGGGGTCTATT-TAACTCAGTATTCAG-3', SEQ ID NO. 24) and ScaI-BP40-Rv (5'-GAGCTCTCAGGTTGCGTACGGGTTTGAGG-3', SEQ ID NO. 25) as primers, and using Prime Star DNA polymerase. This DNA fragment was cloned into pCR-BluntII-TOPO, and the resulting plasmid was designated pCR-ADHBP40-SpeSac.

An ADHNF-pansy F3'5'H#40 DNA fragment obtained by digesting pCR-ADHBP40-SpeSac with SpeI and EcoICRI was ligated with a binary vector fragment obtained by digesting pBI121-Pf3ATp-GUS-Pf3ATt with SalI followed by blunting using Blunting High (Toyobo) and further digesting with XbaI to obtain pBI121-perilla 3ATpro::ADHNF-pansy-F3'5'H#40::perilla 3ATter, and this was transformed in *Agrobacterium tumefaciens* strain EHA105.

Seven recombinant *chrysanthemum* lines of *chrysanthemum* variety Taihei were obtained by using this transformed *Agrobacterium*. Delphinidin was detected in 5 of these lines, and the delphinidin content reached 17.7%.

In addition, pSPB3718 was constructed by inserting an expression cassette of perilla 3ATpro::ADHNF-pansy-F3'5'H#40::perilla 3ATter obtained from pBI121-perilla 3ATpro::ADHNF-pansy-3'5'H#40::perilla 3ATter into pWTT2132 (WO 96/36716), and transformed in *Agrobacterium tumefaciens* strain Agl0. *Chrysanthemum* variety Improved Regan (Seikoen) was transformed by using this transformed *Agrobacterium* strain. 25 lines of recombinant *chrysanthemums* were acquired, and a change in flower color was observed in 7 of these lines. The maximum delphinidin content was 20%.

Example 8 pSFL535 (described in WO 2008/156206) was partially digested with PacI, and a DNA fragment was recovered from which an expression cassette containing pansy F3'5'H gene has been removed. This DNA fragment was ligated with a roughly 3.2 kb DNA fragment obtained by digesting pSFL620 described in Example 4 with PacI to obtain plasmid pSFL635 having the structure shown in FIG. 7. When T-DNA of this plasmid is transfected into a plant, torenia-derived flavone synthase gene and torenia-derived anthocyanin methyltransferase are constitutively expressed, and pansy F3'5'H gene is expected to be specifically expressed in flower petals. This plasmid was transfected into *Agrobacterium* using the method described in WO 2008/156206, and this *Agrobacterium* was transfected into rose variety WKS124 to obtain 83 lines of transformants. The flower petals contained malvidin, petunidin and delphinidin not expressed in WKS124. The total content thereof among all anthocyanidins was an average of 73% and a maximum of 85%. This result indicates that the promoter region derived from pansy BP40 obtained in this experiment (roughly 2.1 kb 5'-untranslated region contained in pSFL514 (BP40pro, SEQ ID NO. 15, see Example 4)) is suitable for expressing exogenous genes in plants, and particularly in roses.

INDUSTRIAL APPLICABILITY

A promoter region thought to govern transcription of enzyme genes in the leaves of perilla, namely a transcriptional regulatory region of perilla anthocyanin 3-acyltransferase gene, was determined to be able to function as a transcriptional regulatory region in flower petals of a different species in the form of *chrysanthemum*. Thus, transcription of exogeneous genes can be specifically induced in tissues such as flowers in which anthocyanins accumulate by using this transcriptional regulatory region of perilla anthocyanin 3-acyltransferase gene. Although examples of transcribed exogenous genes include genes associated with flower color and fragrance, they are not limited thereto.

In addition, the transcriptional regulatory region of pansy-derived F3'5'H gene was also determined to be useful for altering flower color of *chrysanthemum* plants and plants other than *chrysanthemums*.

The invention claimed is:

1. A method for transcribing a nucleic acid in a *chrysanthemum* plant by genetic recombination technology, the method comprising the step of introducing into the *chrysanthemum* plant an expression vector or expression cassette comprising the nucleotide sequence indicated in SEQ ID NO: 1 operably linked to a nucleic acid to be transcribed.

2. The method according to claim 1, wherein the nucleic acid to be transcribed is involved in flavonoid biosynthesis.

3. The method according to claim 1, wherein the nucleic acid to be transcribed is involved in anthocyanin modification.

4. A method for producing a *chrysanthemum* plant wherein expression of perilla anthocyanin 3-acyltransferase is regulated, the method comprising the step of introducing the expression vector or expression cassette of claim 1, wherein said nucleic acid to be transcribed encodes a perilla anthocyanin 3-acyltransferase.

5. The method according to claim 4, wherein the expression vector or the expression cassette contains the nucleotide sequence indicated in SEQ ID NO. 2.

6. A *chrysanthemum* plant cell comprising the expression vector or expression cassette defined in claim 1.

* * * * *